(12) United States Patent
Carney et al.

(10) Patent No.: US 7,935,341 B2
(45) Date of Patent: May 3, 2011

(54) ANTIBODIES TO COMPLEMENTARY PEPTIDES OF THROMBIN OR PORTIONS THEREOF

(75) Inventors: Darrell H. Carney, Galveston, TX (US); John S. Bergmann, Galveston, TX (US); Gerald M. Fuller, Birmingham, AL (US)

(73) Assignee: Orthologic Corp., Tempe, AZ (US)

( * ) Notice: Subject to any disclaimer, the term of this patent is extended or adjusted under 35 U.S.C. 154(b) by 1026 days.

(21) Appl. No.: 11/521,596

(22) Filed: Sep. 14, 2006

(65) Prior Publication Data

US 2008/0241149 A1    Oct. 2, 2008

Related U.S. Application Data

(60) Provisional application No. 60/718,559, filed on Sep. 16, 2005.

(51) Int. Cl.
*A61K 39/00* (2006.01)

(52) U.S. Cl. ............... 424/139.1; 424/133.1; 424/141.1; 424/145.1; 435/331; 514/14.7; 530/387.3; 530/387.9; 530/388.25

(58) Field of Classification Search .................. None
See application file for complete search history.

(56) References Cited

U.S. PATENT DOCUMENTS

| | | | | |
|---|---|---|---|---|
| 5,500,412 | A | * | 3/1996 | Carney et al. .................... 514/13 |
| 5,693,762 | A | * | 12/1997 | Queen et al. ................ 530/387.3 |
| 6,721,663 | B1 | | 4/2004 | Roberts et al. |
| 6,762,166 | B2 | | 7/2004 | Haddox et al. |

FOREIGN PATENT DOCUMENTS

| | | |
|---|---|---|
| WO | WO 03/013569 A2 | 2/2003 |
| WO | WO 03/061690 A1 | 7/2003 |
| WO | WO 2004/014937 A2 | 2/2004 |

OTHER PUBLICATIONS

Bergmann, J.S., et al., "Purification and Characterization of the High Affinity Non-Proteolytically Activated (NPAR) Thrombin Receptor," *Molecular Biology of the Cell* 13(Suppl.): 290A (2002) (From *Abstracts: 42nd American Society for Cell Biology Annaul Meeting*, Abstract No. 1627).

Bergmann, J.S., et al., "Thrombin and Thrombin peptide TP508 (Chrysalin®) Bind to a High Affinity Receptor That Appears to be Larger Than Known Members of the Proteolytically Activated Receptor (PAR) Family," *Molecular Biology of the Cell*, 12(Suppl.): 290A, Abstract No. 1811 (2001).

Blalock, J.E., "Genetic origins of protein shape and interaction rules," *Nature Medicine* 1(9): 876-878 (1995).

Suttnar, J. et al., "Determination of the Putative Binding Sites for Thrombin Receptor Activating Peptide through a Hydropathic Complementary Approach," *Thrombosis Haemostasis* 83(1): 165-170 (2000).

Blalock, J.E., "Complementarity of peptides specified by 'sense' and 'antisense' strands of DNA," *Tibtech* 8: 140-144 (1990).

Bost, K.L., et al., "Similarity between the corticotrophin (ACTH) receptor and a peptide encoded by an RNA that is complementary to ACTH mRNA," *Proc. Natl. Acad. Sci. USA* 82:1372-1375 (1985).

Bost, K.L. and Blalock, J.E., "Production of Anti-idiotypic Antibodies by Immunization with a Pair of Complementary Peptides," *J. Molecular Recognition* 1(4): 179-183 (1989).

Frost, G.H., et al., "Monoclonal Antibody to the Thrombin Receptor Stimulates DNA Synthesis in Combination with Gamma-Thrombin or Phorbol Myristate Acetate," *J. Cell Biology* 105(6): 2551-2558 (1987).

Gho, Y.S. and Chae, C-B., "Anti-angiogenin Activity of the Peptides Complementary to the Receptor-binding Site of Angiogenin," *J. Biological Chemistry* 272(39): 24294-24299 (1997).

* cited by examiner

*Primary Examiner* — Michael Szperka
(74) *Attorney, Agent, or Firm* — Steven G. Davis

(57) ABSTRACT

Disclosed are antibodies and antigen-binding fragments that bind to a complementary peptide having an amino acid sequence that is encoded by the complement of a nucleotide sequence encoding thrombin or a portion thereof. Such antibodies and antigen-binding fragments can be agonists or antagonists of thrombin receptor-mediated events. Also disclosed are methods of using the agonist antibodies and antigen-binding fragments of the invention to activate the non-proteolytically activated thrombin receptor (NPAR) in a subject in need of such treatment. In addition, methods of using the antagonist antibodies and antigen-binding fragments of the invention to inhibit activation of the NPAR in a subject in need of such treatment are disclosed.

11 Claims, 9 Drawing Sheets

Native

```
GCT GGT TAC AAG CCT GAT GAA GGG AAA CGA GGG GAT GCC TGT GAA GGT GAC AGT GGG GGA CCC TTT GTC
 A   G   Y   K   P   D   E   G   K   R   G   D   A   C   E   G   D   S   G   G   P   F   V
```

Complementary 5'-3'

```
CGA CCA ATG TTC GGA CTA CTT CCC TTT GCT CCC CTA CGG ACA CTT CCA CTG TCA CCC CCT GGG AAA CAG
 R   P   M   F   G   L   L   P   F   A   P   L   R   T   L   P   L   S   P   P   G   K   Q
```

Antiparallel Complementary 3'-5'

```
GAC AAA GGG TCC CCC ACT GTC ACC TTC ACA GGC ATC CCC TGC TTT CCC TTC ATC AGG CTT GTA ACC AGC
 D   K   G   S   P   T   V   T   F   T   G   I   P   C   F   P   F   I   R   L   V   T   S
```

FIG. 3

AC-23        n-KGSPTV TFTGIPCFP FIRLVTS-c

23C53        n-KGSPTV TFTGIPSFP FIRLVTS-c

C1053                  n-TFTGIPSFP F-c

ND1053               n-ALTSVPS FAF-c

FIG. 4

```
aattcctcag tgacccagga gctgacacac tatggcgcac gtccgaggct tgcagctgcc   61
tggctgcctg gccctggctg ccctgtgtag ccttgtgcac agccagcatg tgttcctggc  121
tcctcagcaa gcacggtcgc tgctccagcg ggtccggcga gccaacacct tcttggagga  181
ggtgcgcaag ggcaacctag agcgagagtg cgtggaggag acgtgcagct acgaggaggc  241
cttcggggct ctggagtcct ccacggctac ggatgtgttc tgggccaagt acacagcttg  301
tgagacagcg aggacgcctc gagataagct tgctgcatgt ctggaaggta actgtgctga  361
gggtctgggt acgaactacc gagggcatgt gaacatcacc cggtcaggca ttgagtgcca  421
gctatggagg agtcgctacc cacataagcc tgaaatcaac tccactaccc atcctggggc  481
cgacctacag gagaatttct gccgcaaccc cgacagcagc accacgggac cctggtgcta  541
cactacagac cccaccgtga ggaggcagga atgcagcatc cctgtctgtg gccaggatca  601
agtcactgta gcgatgactc cacgctccga aggctccagt gtgaatctgt cacctccatt  661
ggagcagtgt gtccctgatc gggggcagca gtaccagggg cgcctggcgg tgaccacaca  721
tgggctcccc tgcctggcct gggccagcgc acaggccaag gccctgagca agcaccagga  781
cttcaactca gctgtgcagc tggtggagaa cttctgccgc aacccagacg gggatgagga  841
gggcgtgtgg tgctatgtgg ccgggaagcc tggcgacttt gggtactgcg acctcaacta  901
ttgtgaggag gccgtggagg aggagacagg agatgggctg gatgaggact cagacagggc  961
catcgaaggg cgtaccgcca ccagtgagta ccagactttc ttcaatccga ggacctttgg 1021
ctcgggagag gcagactgtg ggctgcgacc tctgttcgag aagaagtcgc tggaggacaa 1081
aaccgaaaga gagctcctgg aatcctacat cgacgggcgc attgtggagg gctcggatgc 1141
agagatcggc atgtcacctt ggcaggtgat gcttttccgg aagagtcccc aggagctgct 1201
gtgtggggcc agcctcatca gtgaccgctg ggtcctcacc gccgcccact gcctcctgta 1261
cccgccctgg acaagaact tcaccgagaa tgaccttctg gtgcgcattg gcaagcactc 1321
ccgcacaagg tacgagcgaa acattgaaaa gatatccatg ttggaaaaga tctacatcca 1381
ccccaggtac aactggcggg agaacctgga ccgggacatt gccctgatga agctgaagaa 1441
gcctgttgcc ttcagtgact acattcaccc tgtgtgtctg cccgacaggg agacggcagc 1501
cagcttgctc caggctggat acaaggggcg ggtgacaggc tggggcaacc tgaaggagac 1561
gtggacagcc aacgttggta aggggcagcc cagtgtcctg caggtggtga acctgcccat 1621
tgtggagcgg ccggtctgca aggactccac ccggatccgc atcactgaca acatgttctg 1681
tgctggttac aagcctgatg aagggaaacg aggggatgcc tgtgaaggtg acagtggggg 1741
accctttgtc atgaagagcc ccttaacaa ccgctggtat caaatgggca tcgtctcatg 1801
gggtgaaggc tgtgaccggg atgggaaata tggcttctac acacatgtgt tccgcctgaa 1861
gaagtggata cagaaggtca ttgatcagtt tggagagtag gggccactca tattctgggc 1921
tcctggaacc aatcccgtga aagaattatt tttgtgtttc taaaactatg gttcccaata 1981
aaagtgactc tcagcgg
```

FIG. 9A

```
MAHVRGLQLPGCLALAALCSLVHSQHVFLAPQQARSLLQRVRRA
NTFLEEVRKGNLERECVEETCSYEEAFGALESSTATDVFWAKYTACETARTPRDKLAA
CLEGNCAEGLGTNYRGHVNITRSGIECQLWRSRYPHKPEINSTTHPGADLQENFCRNP
DSSTTGPWCYTTDPTVRRQECSIPVCGQDQVTAMTPRSEGSSVNLSPPLEQCVPDRG
QQYQGRLAVTTHGLPCLAWASAQAKALSKHQDFNSAVQLVENFCRNPDGDEEGVWCYV
AGKPGDFGYCDLNYCEEAVEEETGDGLDEDSDRAIEGRTATSEYQTFFNPRTFGSEA
DCGLRPLFEKKSLEDKTERELLESYIDGRIVEGSDAEIGMSPWQVMLFRKSPQELLCG
ASLISDRWVLTAAHCLLYPPWDKNFTENDLLVRIGKHSRTRYERNIEKISMLEKIYIH
PRYNWRENLDRDIALMKLKKPVAFSDYIHPVCLPDRETAASLLQAGYKGRVTGWGNLK
ETWTANVGKGQPSVLQVVNLPIVERPVCKDSTRIRITDNMFCAGYKPDEGKRGDACEG
DSGGPFVMKSPFNNRWYQMGIVSWGEGCDRDGKYGFYTHVFRLKKWIQKVIDQFGE
```

ANTIBODIES TO COMPLEMENTARY PEPTIDES OF THROMBIN OR PORTIONS THEREOF

RELATED APPLICATION

This application claims the benefit of U.S. Provisional Application No. 60/718,559, filed on Sep. 16, 2005. The entire teachings of the above application are incorporated herein by reference.

BACKGROUND OF THE INVENTION

Thrombin is an important serine protease in hemostasis and thrombosis, and is present in blood plasma in the form of a precursor, pro-thrombin. One of the key actions of thrombin is cellular modulation via receptor activation. A functional human thrombin receptor (PAR-1), which was cloned in 1991 (Vu, T. K., et al., Cell 64(6):1057-68 (1991)), was found to be a member of the G-protein coupled receptor (GPCR) superfamily. Receptor activation of PAR-1 putatively occurs by N-terminal recognition and proteolytic cleavage at the Arg-41/Ser-42 peptide bond to reveal a truncated N-terminus. This new N-terminus, acting as a tethered ligand to recognize a site on the receptor, can trigger activation and signal transduction leading to platelet aggregation. Since 1991, three other protease-activated receptors with extensive homology to this thrombin receptor, namely "PAR-2" (Nystedt, S., et al., Proc. Natl. Acad. Sci. USA 91:9208-12 (1994)), "PAR-3" (Ishihara, H., et al., Nature 386(6624):502-06 (1997)), and "PAR-4" (Xu, W. F., et al., Proc. Natl. Acad. Sci. USA 95(12):6642-46 (1998)), have been cloned. Thrombin receptor (PAR-1) specific antibody-induced blockade of the platelet thrombin receptor has shown efficacy against arterial thrombosis in vivo (Cook, J. J., et al., Circulation 91(12):2961-71 (1995)). Hence, antagonists of the thrombin receptor (PAR-1) are useful to block these protease-activated receptors and, as such, may be used to treat platelet-mediated thrombotic disorders, such as myocardial infarction, stroke, restenosis, angina, atherosclerosis, and ischemic conditions.

Although particular protease-activated receptors (e.g., PAR-1, PAR-2, PAR-3 and PAR-4) have been identified, thrombin also possesses growth-promoting activity for a wide variety of cells from various tissues, which results from activation of a specific cell surface receptor known as the non-proteolytically activated thrombin receptor (NPAR) (Horvat, R., et. al., J. Cell Sci. 108, 1155-64 (1995)). For example, thrombin has been shown to promote angiogenesis, the development of new blood vessels, and to stimulate endothelial cell proliferation (see, e.g., U.S. Pat. Nos. 5,352,664 and 5,500,412; the contents of both of which are incorporated herein by reference in their entirety). To date, this NPAR has not been cloned or characterized at the molecular level.

The discovery that protein sequences encoded by complementary strands of nucleic acids can bind to one another is known as the molecular recognition theory (MRT) (Blalock, Nature Medicine 1:876-878 (1995)). This theory, which is based on the development of complementary peptides (CPs) specified by ligand antisense RNA, has proven useful in designing interactive peptides, isolating receptors, and producing anti-receptor and anti-idiotypic antibodies (see, e.g., Blalock, et al., Trends Biotechnol. 8:140-144 (1990); and Clarke, et al., In: Antisense Nucleic Acids and Proteins: Fundamentals and Applications vandrol Krol, A. V., and Mol, J. N. M. (eds): Dekker, New York: 169-186 (1991)). Antibodies to particular CPs have been used to identify specific receptors that have been difficult to purify.

Given the importance of thrombin in such diverse processes as mitogenesis, cell growth, wound healing, tissue adhesion, angiogenesis and tumor metastasis, it would be useful to have new molecules that can stimulate or inhibit one or more thrombin functions. It would also be useful to identify NPAR, which is expressed on a wide variety of cells, and is involved in thrombin-induced growth-promoting activity.

SUMMARY OF THE INVENTION

It has now been discovered that antibodies or antigen-binding fragments thereof that bind to a complementary peptide that is encoded by the complement of a nucleotide sequence encoding thrombin or a portion thereof can be agonists or antagonists of non-proteolytically activated thrombin receptor (NPAR)-mediated events. Because thrombin is involved in a number of bioregulatory effects, the present invention, which allows one to selectively promote or inhibit these effects, has a number of clinical applications.

In one embodiment, the invention is an antibody or antigen-binding fragment thereof that binds to a complementary peptide encoded by the complement of a nucleotide sequence encoding a portion of thrombin. In another embodiment, the portion of thrombin (which is encoded by the sense or +RNA strand and is the complement of the antisense or −RNA strand that encodes the complementary peptide to which the antibody or antigen-binding fragment binds) is a portion of a mammalian thrombin. In a particular embodiment, the portion of thrombin is a portion of a human thrombin.

In one embodiment, the complementary peptide is encoded by the complement of a nucleotide sequence encoding a thrombin receptor binding domain or a portion thereof. In a particular embodiment, the thrombin receptor binding domain has the amino acid sequence AGYKPDEGKRG-DACEGDSGGPFV (i.e., amino acids 508-530 of human pro-thrombin (SEQ ID NO:1)). In another embodiment, the portion of the thrombin receptor binding domain has the amino acid sequence EGKRGDACEG (i.e., amino acids 514-523 of human pro-thrombin (SEQ ID NO:2)).

As described herein, complementary peptides of domains of thrombin that are encoded by both the 5'-3' sequence of the antisense RNA strand and the 3'-5' sequence of the antisense RNA strand can be used to produce the antibodies and antigen-binding domains of the invention. Therefore, in one embodiment, the complementary peptide (to which the antibodies and antigen-binding fragments of the invention bind) is encoded by the 5'-3' sequence of the antisense RNA strand. In another embodiment, the complementary peptide is encoded by the 3'-5' sequence of the antisense RNA strand.

In particular embodiments, the complementary peptides (to which the antibodies and antigen-binding fragments of the invention bind) have an amino acid sequence selected from the group consisting of KGSPTVTFTGIPCFPFIRLVTS (AC-23 (SEQ ID NO:3)), KGSPTVTFTGIPSFPFIRLVTS (23C53 (SEQ ID NO:4)), TFTGIPSFPF (C1053 (SEQ ID NO:5)), RPMFGLLPFAPLRTLPLSPPGKQ (AC-23rev, which is the complementary 5'-3' peptide corresponding to AC-23 (SEQ ID NO:6)) and LPFAPLRTLP (C1053rev, which is the complementary 5'-3' peptide corresponding to C1053 (SEQ ID NO:7)).

In one embodiment, the antibody or antigen-binding fragment of the invention is an agonist antibody or antigen-binding fragment thereof. In another embodiment, the antibody or antigen-binding fragment of the invention is an antagonist antibody or antigen-binding fragment thereof. In other embodiments, the antibody is a polyclonal antibody, a monoclonal antibody or antigen-binding fragment thereof, a human antibody or antigen-binding fragment thereof, a humanized antibody or antigen-binding fragment thereof, or a chimeric antibody or antigen-binding fragment thereof. In one embodiment, the antibody or antigen-binding fragment is an antigen-binding fragment (e.g., an Fab fragment, an Fab' fragment, an F(ab')$_2$ fragment or an Fv fragment).

In another embodiment, the antibody or antigen-binding fragment thereof binds to a cysteine-altering complementary peptide having the amino acid sequence KGSPTVTFTGIPS-FPFIRLVTS (23C53 (SEQ ID NO:4)).

In one embodiment, the invention is a cell that produces an antibody or antigen-binding fragment thereof that binds to a complementary peptide encoded by the complement of a nucleotide sequence encoding a portion of thrombin.

In another embodiment, the invention is a pharmaceutical composition comprising an antibody or antigen-binding fragment thereof and a pharmaceutically-acceptable carrier, wherein the antibody or antigen-binding fragment binds to a complementary peptide encoded by the complement of a nucleotide sequence encoding a portion of thrombin.

In another embodiment, the invention is a method of activating the non-proteolytically activated thrombin receptor (NPAR) in a subject in need of such treatment, comprising administering an effective amount of an antibody or antigen-binding fragment thereof to the subject, wherein the antibody or antigen-binding fragment:
  i) is an agonist antibody or antigen-binding fragment thereof; and
  ii) binds to a complementary peptide encoded by the complement of a nucleotide sequence encoding a portion of thrombin.
In particular embodiments, the subject in need of such treatment is in need of treatment to promote cartilage growth or repair, to promote growth of bone, to promote wound healing (e.g., for a chronic wound), or to promote cardiac repair and/or inhibit restenosis.

In other embodiments, the antagonist antibodies and antigen-binding fragments of the invention, which bind to a complementary peptide encoded by the complement of a nucleotide sequence encoding a portion of thrombin, are used for particular indications. Thus, in one embodiment, the invention is a method of inhibiting tumor cell growth in a subject in need of such treatment, comprising administering an effective amount of an antagonist antibody or antigen-binding fragment of the invention. In another embodiment, the invention is a method of inhibiting angiogenesis in a subject in need of such treatment, comprising administering an effective amount of an antagonist antibody or antigen-binding fragment of the invention. In another embodiment, the invention is a method of inhibiting scar formation or tissue adhesion in, or on, a subject in need thereof, comprising administering an effective amount of an antagonist antibody or antigen-binding fragment of the invention. In yet another embodiment, the invention is a method of antagonizing thrombin receptor activity in a subject in need thereof, comprising administering an effective amount of an antagonist antibody or antigen-binding fragment of the invention. In still another embodiment, the invention is a method of inhibiting thrombin-mediated mitogenesis in a subject in need thereof, comprising administering an effective amount of an antagonist antibody or antigen-binding fragment of the invention. In a further embodiment, the invention is a method of inhibiting thrombin-mediated fibroblast proliferation in a subject in need of such inhibition, comprising administering an effective amount of an antagonist antibody or antigen-binding fragment of the invention In one embodiment, the invention is a method of detecting the non-proteolytically activated thrombin receptor (NPAR) comprising:
  a) contacting a sample with an antibody or antigen-binding fragment of the invention, under conditions suitable for binding of the antibody or antigen-binding fragment to said NPAR present in the sample; and
  b) detecting antibody-NPAR complexes or antigen-binding fragment-NPAR complexes,
wherein detection of the antibody-NPAR complexes or antigen-binding fragment-NPAR complexes is indicative of the presence of NPAR in the sample. In a particular embodiment, the antibody or antigen-binding fragment comprises a detectable label.

In one embodiment, the invention is a method of detecting and/or identifying an agent that binds to the non-proteolytically activated thrombin receptor (NPAR). In the method, an antibody or antigen-binding fragment of the invention, a test agent, and a composition comprising NPAR, are combined, and the formation of a complex between the antibody or antigen-binding fragment and NPAR is detected or measured. A decrease in the formation of the complex, relative to a suitable control, indicates that the test agent binds to NPAR.

BRIEF DESCRIPTION OF THE DRAWINGS

FIG. 1 shows a region of the +RNA strand (SEQ ID NO:8) and –RNA strand (SEQ ID NO:9) for a hypothetical RNA, and the encoded peptides (ATCH (SEQ ID NO:10) and HTCA (SEQ ID NO:11)) for each of these strands. The graph on the right is a hydropathy plot of the two complementary peptides (CPs). Also on the right is a schematic showing complementary structures of the ligand and receptor, as well as complementary structures of the binding domains of antibodies to the ligand and receptor.

FIG. 3 depicts the nucleotide (SEQ ID NO:12) and amino acid (SEQ ID NO:1) sequences of TP508 (labeled as "Native"), the nucleotide (SEQ ID NO:13) and amino acid (SEQ ID NO:14) sequences of its complementary peptide generated in the 5'-3' direction (labeled as "Complementary 5'-3'), and the nucleotide (SEQ ID NO:15) and amino acid (SEQ ID NO:16) sequences of its complementary peptide generated in the 3'-5' direction (labeled as "Antiparallel Complementary 3'-5').

FIG. 4 depicts the 5'-3' amino acid sequence of particular CPs to the thrombin binding domain. In particular, the amino acid sequences of the complementary peptides AC-23 (SEQ ID NO:3), 23C53 (SEQ ID NO:4), C1053 (SEQ ID NO:5) and ND1053 (SEQ ID NO:17) are depicted. AC-23, 23C53 and C1053 are CPs that are derived from the thrombin receptor binding domain of human thrombin, while ND1053 is a CP that is derived from the thrombin receptor binding domain of bovine thrombin.

FIG. 9A depicts the nucleotide sequence of human pro-thrombin (SEQ ID NO:18); GenBank Accession No. AJ972449.

FIG. 9B depicts the encoded amino acid sequence of human pro-thrombin (SEQ ID NO:19). Amino acids 508-530, which contain the thrombin receptor binding domain, are underlined.

DETAILED DESCRIPTION OF THE INVENTION

Figure 1:
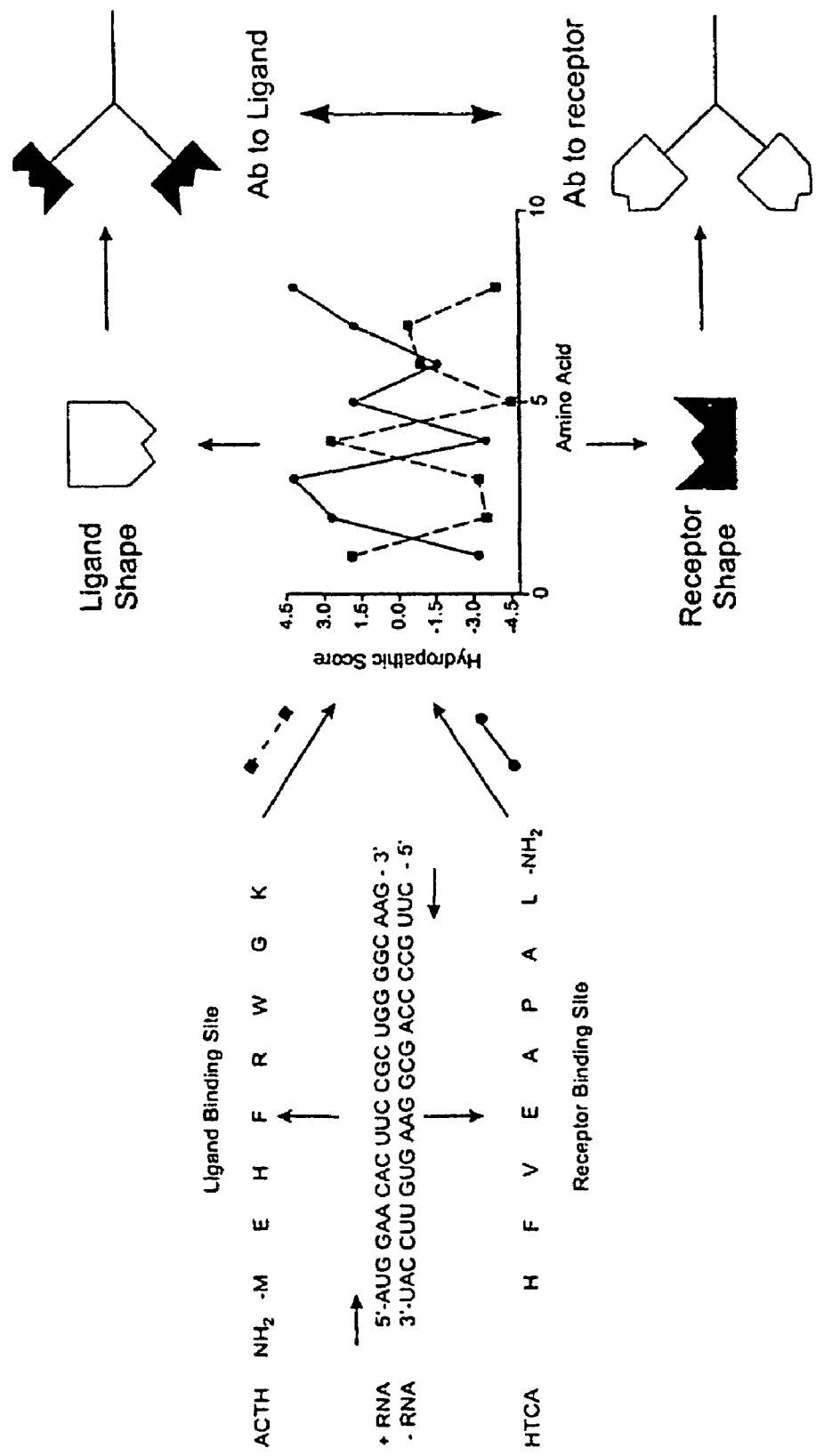
FIG. 1 is a schematic depicting the Molecular Recognition Theory. Specifically.
Figure 2:
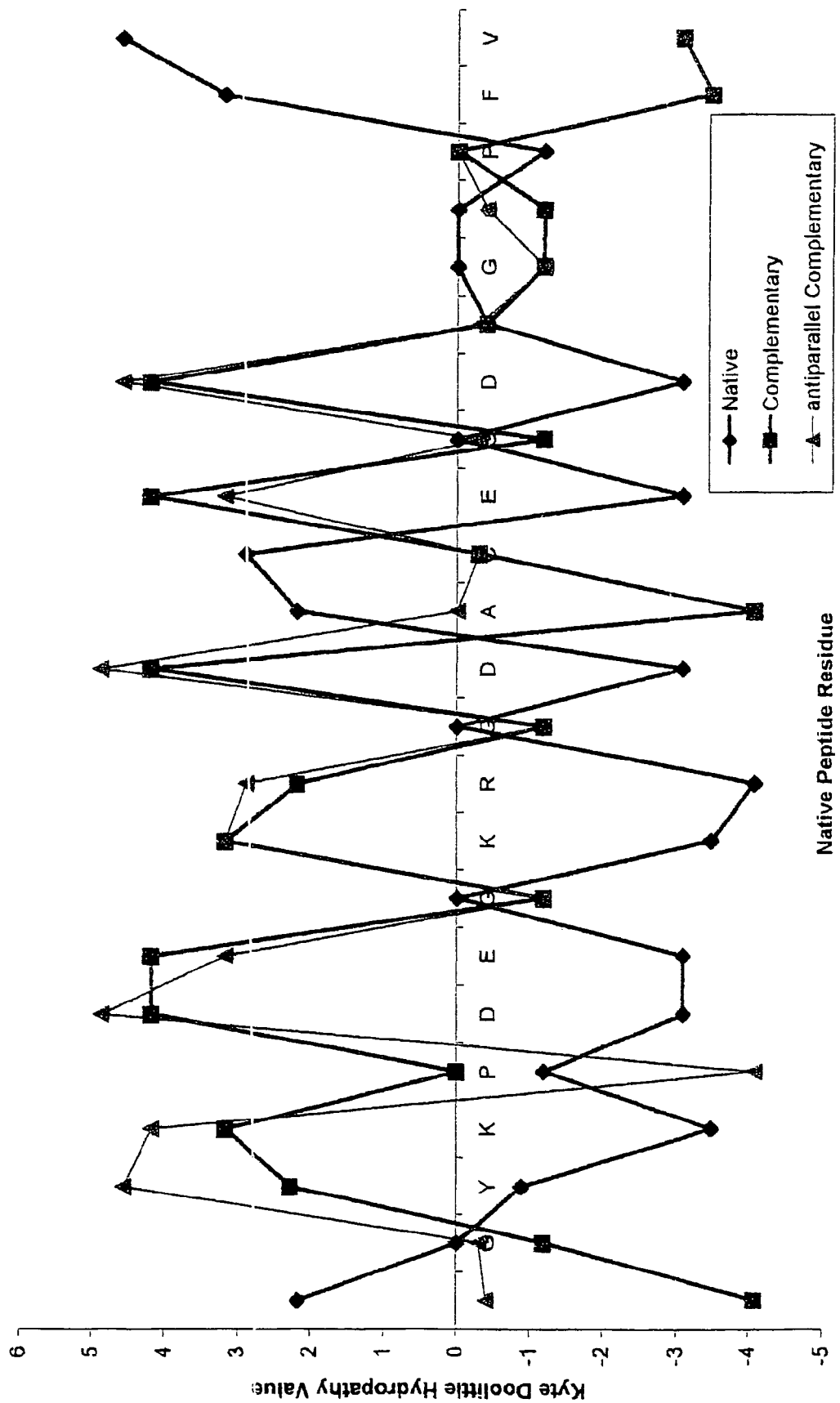
FIG. 2 is a Kyte Doolittle Hydropathy Plot for TP508 (labeled as "Native"; SEQ ID NO:1) and its complementary peptide (the complementary peptide to TP508 that is generated in the 5'-3' direction) and antiparallel complementary peptide (the complementary peptide to TP508 that is generated in the 3'-5' direction).

A description of preferred embodiments of the invention follows.

While this invention has been particularly shown and described with references to preferred embodiments thereof, it will be understood by those skilled in the art that various changes in form and details may be made therein without departing from the scope of the invention encompassed by the appended claims.

Thrombin

Thrombin, a molecule once considered important only in the context of blood coagulation, has now been shown to mediate a number of potent biological effects that are not directly related to coagulation. Many of these effects are due, at least in part, to signals generated by the interaction between thrombin or thrombin-like molecules and the high-affinity thrombin receptors present on the surface of many cells.

As is known in the art, particular thrombin peptide fragments and derivatives are able to either mimic or inhibit thrombin-mediated events (see, e.g., U.S. Pat. Nos. 5,500,412 and 5,352,664; the entire teachings of both of which are incorporated herein by reference). Thrombin peptide derivatives are synthetic analogs of thrombin that have an amino acid sequence derived at least in part from that of thrombin and are active at the non-proteolytically activated thrombin receptor.

U.S. Pat. Nos. 5,500,412 and 5,352,664 describe both stimulatory (agonistic) thrombin polypeptide derivatives and inhibitory (antagonistic) thrombin polypeptide derivatives. Both the stimulatory (agonistic) thrombin polypeptide derivatives and inhibitory (antagonistic) thrombin polypeptide derivatives possess a thrombin receptor binding domain that includes a segment of the polypeptide that is capable of selectively binding to the high-affinity thrombin receptor. This segment of the polypeptide contains a domain (represented by residues 517-520 of human prothrombin) with a sequence homologous to the tripeptide cell binding domain of fibronectin, [Arg-Gly-Asp]. This tripeptide sequence is common to a number of proteins that may interact with cells (reviewed by Ruoslahti and Peirschbacher, Cell 44:517-18 (1985)). Moreover, it has been shown that a peptide representing amino acid residues 517-520 of human prothrombin (p517-520) and peptides representing amino acid residues 516-522 and 510-526 of human prothrombin (p1516-522 and p510-526, respectively) are able to promote fibroblast attachment, which is comparable to that induced by fibronectin-specific peptides.

In addition to the thrombin receptor binding domain, the stimulatory (agonistic) thrombin polypeptide derivatives possess a domain (represented by amino acid residues 519-530 of human prothrombin) with a high degree of homology to a number of serine esterases. However, the inhibitory (antagonistic) thrombin polypeptide derivatives do not include the serine esterase domain.

Thrombin peptide derivatives from amino acid residues 508-530 of human pro-thrombin have been described for promoting thrombin receptor mediated cell stimulation and for their use in the treatment of wounds, stimulating bone growth and cartilage growth or repair, and promoting cardiac tissue repair (see, e.g., U.S. Pat. Nos. 5,352,664, 5,500,412, WO 02/07748, WO 02/005836, WO 02/004008 and WO 03/013569; the contents of each of which are incorporated herein by reference in their entirety). In addition, stimulatory (agonistic) thrombin polypeptide derivatives containing both fibronectin- and serine protease-homologous domains (residues 508 to 530 of human prothrombin) bind to thrombin receptors with high-affinity and substitute for DIP-alpha-thrombin as an initiator of receptor occupancy-related mitogenic signals. In contrast, inhibitory (antagonistic) thrombin polypeptide derivatives containing only the fibronectin-homologous domain (p1517-520) (but not the serine protease-homologous domain) bind to the thrombin receptor without inducing mitogenesis. An intermediate thrombin peptide derivative (p159-530) retains the ability to mediate mitogenesis but to a much lesser degree than p508-530.

Molecular Recognition Theory

Blalock and Smith (1984) observed that the hydropathic character of an amino acid residue is related to the identity of the middle letter of the triplet codon from which it is transcribed (Blalock, J. E., and Smith, E. M., *Biochem. Biophys. Res. Commun.* 12: 203-07 (1984)). Specifically, a triplet codon with thymine (T) as its middle base codes for a hydrophobic residue while adenine (A) codes for a hydrophilic residue. A triplet codon with middle bases cytosine (C) or guanine (G) encode residues that are relatively neutral and with similar hydropathy scores. Hydropathy is an index of the affinity of an amino acid for a polar environment; hydrophilic residues yielding a more negative score, while hydrophobic residues exhibit more positive scores. Kyte and Doolittle (1982) conceived a hydropathy scale that is widely used (Kyte, J., and Doolittle, R. F., *J. Mol. Biol.* 5:105-32 (1982)). The observed relationship between the middle base of a triplet codon and residue hydropathy entails that peptides encoded by complementary DNA will exhibit complementary, or inverted, hydropathic profiles. It was proposed that because two peptide sequences encoded in complementary DNA strands display inverted hydropathic profiles, they may form amphipathic secondary structures, and bind to one another (Bost, K. L., et al., *Proc. Natl. Acad. Sci. USA* 82:1372-75 (1985)). Complementary peptides have been reported to form binding complexes with their "sense" peptide counterparts for a number of different systems (Root-Bernstein, R. S., and Holsworthy, D. D., *J. Theor. Biol.* 190:107-19 (1988)). For example, Gho and Chae describe peptide antagonists of human angiogenin that are complementary peptides encoded by the antisense RNA sequence corresponding to the receptor binding site of angiogenin (Gho, Y. S, and Chae, C. B. *J. Biol. Chem.* 272(39):24294-99 (1997)). Ghiso et al. describe a peptide complementary to a region of cystatin C that exhibits inhibitory activity (Ghiso, J., et al., *Proc. Natl. Acad. Sci. USA* 87(4):1288-91 (1990)), and Bost and Blalock describe the production of anti-idiotypic antibodies by immunization with a pair of complementary peptides (Bost, K. L., and Blalock, J. E., *J. Molec. Recognit.* 1:179-83 (1989)).

The scope of this analysis for explaining the interactions between proteins was further developed by Blalock to propose a *Molecular Recognition Theory* (MRT) (Bost, K. L., et al., *Proc. Natl. Acad. Sci. USA* 82:1372-75 (1985); Blalock, J. E., *Nature Med.* 1:876-78 (1995)). This theory suggests that a "molecular recognition" code of interaction exists between peptides that are encoded by complementary strands of DNA, based on the observation that such peptides will exhibit inverted hydropathic profiles. Although MRT has proved successful for predicting particular binding interactors, the theory has not received widespread scientific recognition.

Blalock suggested that it is the linear pattern of amino acid hydropathy scores in a sequence (rather than the combination of specific residue identities), that defines the secondary structure environment. Furthermore, he suggested that sequences with inverted hydropathic profiles are complementary in shape by virtue of inverse forces that determine their steric relationships.

Deriving a Complementary Peptide in the 3'-5' Reading Frame

As a corollary to his original work, Blalock contended that as well as reading a complementary codon in the usual 5'-3' direction, reading a complementary codon in the 3'-5' direction would also yield amino acid sequences that displayed opposite hydropathic profiles (Bost, K. L., et al., *Proc. Natl. Acad. Sci. USA* 82:1372-75 (1985)). This follows from the observation that the middle base of a triplet codon determines the hydropathy index of the residue it codes for, and therefore reading a codon in the reverse direction may change the identity, but not the hydropathic nature of the coded amino acid (Table 1).

TABLE 1

The relationships between amino acids and the residues encoded in the complementary strand
The relationships between amino acids and the residues encoded in the complementary strand reading 3'-5'

| Amino Acid | Codon | Complementary codon | Complementary Amino acid | Amino Acid | codon | Complementary codon | Complementary Amino acid |
|---|---|---|---|---|---|---|---|
| Alanine | GCA | CGU | Arginine | Serine | UCA | AGU | Serine |
| | GCG | CGC | | | UCC | AGQ | Arginine |
| | GCC | CGG | | | UCG | AGC | Serine |
| | GCU | CGA | | | UCU | AGA | Arginine |
| | | | | | AGC | UCG | Serine |
| | | | | | AGU | UCA | Serine |
| Arginine | CGG | GCC | Alanine | Glutamine | CAA | GUU | Valine |
| | CGA | GCU | Alanine | | CAG | GUC | Valine |
| | CGC | GCG | Alanine | | | | |
| | CGU | GCA | Alanine | | | | |
| | AGG | UCC | Serine | | | | |
| | AGA | UCU | Serine | | | | |
| Aspartic Acid | GAC | GUC | Valine | Glycine | GGA | CCU | Proline |
| | GAU | AUC | Isoleucine | | GGC | CCG | Proline |
| | | | | | GGU | CCA | Proline |
| | | | | | GGG | CCC | Proline |
| Asparagine | AAC | UUG | Leucine | Histidine | CAC | GUG | Valine |
| | AAU | UUA | Leucine | | CAU | GUA | Valine |
| Cysteine | UGU | ACA | Threonine | Isoleucine | AUA | UAU | Tyrosine |
| | UGC | ACG | Threonine | | AUC | UAG | Stop |
| | | | | | AUU | UAA | Stop |
| Glutamic Acid | GAA | CUU | Leucine | Leucine | CUG | GAC | Asp |
| | GAG | CUG | Leucine | | CUC | GAG | Glutamic acid |
| | | | | | CUU | GAA | |
| | | | | | UUA | AAU | Glutamic Acid |
| | | | | | CUA | GAU | |
| | | | | | UUG | AAC | Asparagine |
| | | | | | CUG | GAC | Aspartic Acid Asparagine Aspartic Acid |

TABLE 1-continued

The relationships between amino acids and the residues encoded
in the complementary strand
The relationships between amino acids and the residues encoded
in the complementary strand reading 3'-5'

| Amino Acid | Codon | Complementary codon | Complementary Amino acid | Amino Acid | codon | Complementary codon | Complementary Amino acid |
|---|---|---|---|---|---|---|---|
| Lysine | AAA | UUU | Phenylalanine | Threonine | ACA | UGU | Cysteine |
| | AAG | UUC | Phenylalanine | | ACG | UGC | Cysteine |
| | | | | | ACC | UGG | Tryptophan |
| | | | | | ACU | UGA | Stop |
| Methionine | AUG | UAC | Tyrosine | Tryptophan | UGG | ACC | Threonine |
| Phenylalanine | UUU | AAA | Lysine | Tyrosine | UAC | AUG | Methionine |
| | UUC | AAG | Lysine | | UAU | AUA | Isoleucine |
| Proline | CCA | GGU | Glycine | Valine | GUA | CAU | Histidine |
| | CCC | GGG | Glycine | | GUG | CAC | Histidine |
| | CCU | GGA | Glycine | | GUC | GAG | Glutamine |
| | CCG | GGC | Glycine | | GUU | CAA | Glutamine |

Antibodies and Antibody Producing Cells

In one embodiment, the present invention encompasses antibodies or antigen-binding fragments thereof that bind to the complementary peptides of the invention. The antibodies of the invention can be polyclonal or monoclonal, and the term "antibody" is intended to encompass both polyclonal and monoclonal antibodies. The terms polyclonal and monoclonal refer to the degree of homogeneity of an antibody preparation, and are not intended to be limited to particular methods of production. In one embodiment, the antibody or antigen-binding fragment is a monoclonal antibody or antigen-binding fragment thereof. The term "monoclonal antibody" or "monoclonal antibody composition" as used herein, refers to a population of antibody molecules that contain only one species of an antigen binding site capable of immunoreacting with a particular epitope of a polypeptide of the invention. A monoclonal antibody composition thus typically displays a single binding affinity for a particular polypeptide of the invention with which it immunoreacts.

The term "antibody" as used herein also encompasses functional fragments of antibodies, including fragments of chimeric, humanized, primatized, veneered or single chain antibodies. Functional fragments include antigen-binding fragments of antibodies that bind to the complementary peptides of the invention. For example, antibody fragments capable of binding to a complementary peptide of the invention, include, but are not limited to Fv, Fab, Fab' and F(ab')$_2$ fragments. Such fragments can be produced by enzymatic cleavage or by recombinant techniques. For example, papain or pepsin cleavage can generate Fab or F(ab')$_2$ fragments, respectively. Other proteases with the requisite substrate specificity can also be used to generate Fab or F(ab')$_2$ fragments. Antibodies can also be produced in a variety of truncated forms using antibody genes in which one or more stop codons have been introduced upstream of the natural stop site. For example, a chimeric gene encoding a F(ab')$_2$ heavy chain portion can be designed to include DNA sequences encoding the CH$_1$ domain and hinge region of the heavy chain.

Single chain antibodies, and chimeric, humanized or primatized (CDR-grafted), or veneered antibodies, as well as chimeric, CDR-grafted or veneered single chain antibodies, comprising portions derived from different species, and the like are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. See also, Newman, R. et al., *BioTechnology*, 10: 1455-1460 (1992), regarding primatized antibody, and Ladner et al., U.S. Pat. No. 4,946,778 and Bird, R. E. et al., *Science*, 242: 423-426 (1988)) regarding single chain antibodies.

Humanized antibodies can be produced using synthetic or recombinant DNA technology using standard methods or other suitable techniques. Nucleic acid (e.g., cDNA) sequences coding for humanized variable regions can also be constructed using PCR mutagenesis methods to alter DNA sequences encoding a human or humanized chain, such as a DNA template from a previously humanized variable region (see e.g., Kamman, M., et al., *Nucl. Acids Res.*, 17: 5404 (1989)); Sato, K., et al., *Cancer Research*, 53: 851-856 (1993); Daugherty, B. L. et al., *Nucleic Acids Res.*, 19(9): 2471-2476 (1991); and Lewis, A. P. and J. S. Crowe, *Gene*, 101: 297-302 (1991)). Using these or other suitable methods, variants can also be readily produced. In one embodiment, cloned variable regions can be mutated, and sequences encoding variants with the desired specificity can be selected (e.g., from a phage library; see e.g., Krebber et al., U.S. Pat. No. 5,514,548; Hoogenboom et al., WO 93/06213).

The antibody can be a humanized antibody comprising one or more immunoglobulin chains (e.g., an antibody comprising a CDR of nonhuman origin (e.g., one or more CDRs derived from an antibody of nonhuman origin) and a framework region derived from a light and/or heavy chain of human origin (e.g., CDR-grafted antibodies with or without framework changes)). In one embodiment, the antibody or antigen-binding fragment thereof comprises the light chain CDRs (CDR1, CDR2 and CDR3) and heavy chain CDRs (CDR1, CDR2 and CDR3) of a particular immunoglobulin. In another embodiment, the antibody or antigen-binding fragment further comprises a human framework region.

The antibodies described herein can also be conjugated to an agent. In one embodiment, the agent is a label, for example, a radioisotope, an epitope label (tag), an affinity label (e.g., biotin, avidin), a spin label, an enzyme, a fluorescent group or a chemiluminescent group. Labeled antibodies or antigen-binding fragments of the present invention can be used, e.g., in the screening and diagnostic methods described herein. In another embodiment, the antibody is conjugated to a drug, toxin or anti-inflammatory agent. Conjugation of a drug, toxin or anti-inflammatory agent to the antibodies and antigen-binding fragments of the invention allows for targeting of these agents to sites of thrombin receptor expression and/or activity. Drugs and toxins that can be conjugated to the antibodies of the present invention include, for example, chemotherapeutic agents (e.g., mitomycin C, paxlitaxol, methotrexate, 5-fluorouracil, cisplatin, cyclohexamide) and toxins (e.g., ricin, gelonin). Other suitable agents for targeting to sites of thrombin receptor expression and/or activity are known to those of skill in the art.

Antibodies that are specific for a complementary peptide of the invention can be raised against an appropriate immunogen, such as a synthetic or recombinant complementary peptide or a portion thereof. Antibodies can also be raised by immunizing a suitable host (e.g., mouse) with transfected cells that express a complementary peptide. Such cells can also be used in a screen for an antibody that binds thereto (See e.g., Chuntharapai et al., *J. Immunol.*, 152: 1783-1789 (1994); Chuntharapai et al., U.S. Pat. No. 5,440,021).

Preparation of Immunizing Antigen, and Polyclonal and Monoclonal Antibody production can be performed using any suitable technique (e.g., as exemplified herein). A variety of methods have been described (see e.g., Kohler et al., *Nature*, 256: 495-497 (1975) and *Eur. J. Immunol.* 6: 511-519 (1976); Milstein et al., *Nature* 266: 550-552-(1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer '94), Ausubel, F. M. et al., Eds., (John Wiley & Sons: New York, N.Y.), Chapter 11, (1991)). Generally, a hybridoma is produced by fusing a suitable immortal cell line (e.g., a myeloma cell line, such as SP2/0, P3X63Ag8.653 or a heteromyeloma) with antibody-producing cells. Antibody-producing cells can be obtained from the peripheral blood or, preferably the spleen or lymph nodes, of humans or other suitable animals immunized with the antigen of interest (e.g., a complementary peptide). The fused cells (hybridomas) can be isolated using selective culture conditions, and cloned by limiting dilution. Cells that produce antibodies with the desired specificity can be selected by a suitable assay (e.g., ELISA).

Other suitable methods of producing or isolating antibodies of the requisite specificity (e.g., human antibodies or antigen-binding fragments) can be used, including, for example, methods that select recombinant antibody from a library (e.g., a phage display library). Transgenic animals capable of producing a repertoire of human antibodies (e.g., Xenomouse® (Abgenix, Fremont, Calif.)) can be produced using suitable methods (see e.g., Jakobovits et al., *Proc. Natl. Acad. Sci. USA*, 90: 2551-2555 (1993); Jakobovits et al., *Nature*, 362: 255-258 (1993)). Additional methods that are suitable for production of transgenic animals capable of producing a repertoire of human antibodies have been described (e.g., Lonberg et al., U.S. Pat. No. 5,545,806; Surani et al., U.S. Pat. No. 5,545,807; Lonberg et al., WO 97/13852).

The invention also encompasses bispecific antibodies, or functional fragments thereof (e.g., $F(ab')_2$), which bind to a complementary peptide of the invention and at least one other antigen (e.g., a tumor antigen, a viral antigen). Bispecific antibodies can be secreted by triomas and hybrid hybridomas. Generally, triomas are formed by fusion of a hybridoma and a lymphocyte (e.g., antibody-secreting B cell) and hybrid hybridomas are formed by fusion of two hybridomas. Each of the fused cells (i.e., hybridomas, lymphocytes) produces a monospecific antibody. However, triomas and hybrid hybridomas can produce an antibody containing antigen-binding sites that recognize different antigens. The supernatants of triomas and hybrid hybridomas can be assayed for bispecific antibody using a suitable assay (e.g., ELISA), and bispecific antibodies can be purified using conventional methods. (see, e.g., U.S. Pat. No. 5,959,084 (Ring et al.), U.S. Pat. No. 5,141,736 (Iwasa et al.), U.S. Pat. Nos. 4,444,878, 5,292,668, 5,523,210 (all to Paulus et al.) and U.S. Pat. No. 5,496,549 (Yamazaki et al.)).

In one embodiment, the invention relates to an isolated cell that produces an antibody or an antigen-binding fragment of the invention. In a particular embodiment, the isolated antibody-producing cell of the invention is an immortalized cell, such as a hybridoma, heterohybridoma, lymphoblastoid cell or a recombinant cell. The antibody-producing cells of the present invention have uses other than for the production of antibodies. For example, the cell of the present invention can be fused with other cells (such as suitably drug-marked human myeloma, mouse myeloma, human-mouse heteromyeloma or human lymphoblastoid cells) to produce, for example, additional hybridomas, and thus provide for the transfer of the genes encoding the antibody. In addition, the cell can be used as a source of nucleic acids encoding the anti-complementary peptide immunoglobulin chains, which can be isolated and expressed (e.g., upon transfer to other cells using any suitable technique (see e.g., Cabilly et al., U.S. Pat. No. 4,816,567, Winter, U.S. Pat. No. 5,225,539)). For instance, clones comprising a sequence encoding a rearranged anti-complementary peptide light and/or heavy chain can be isolated (e.g., by PCR). In addition, cDNA libraries can be prepared from mRNA isolated from an appropriate cell line, and cDNA clones encoding an anti-HMGB immunoglobulin chain(s) can be isolated. Thus, nucleic acids encoding the heavy and/or light chains of the antibodies, or portions thereof, can be obtained and used for the production of the specific immunoglobulin, immunoglobulin chain, or variants thereof (e.g., humanized immunoglobulins) in a variety of host cells or in an in vitro translation system. For example, the nucleic acids, including cDNAs, or derivatives thereof encoding variants, such as a humanized immunoglobulin or immunoglobulin chain, can be placed into suitable prokaryotic or eukaryotic vectors (e.g., expression vectors) and introduced into a suitable host cell by an appropriate method (e.g., transformation, transfection, electroporation, infection), such that the nucleic acid is operably linked to one or more expression control elements (e.g., in the vector or integrated into the host cell genome), to produce a recombinant antibody-producing cell. Thus, in certain embodiments, the invention is a nucleic acid that encodes an antibody or antigen-binding fragment of the invention. In other embodiments, the invention is a vector that comprises a nucleic acid encoding an antibody or antigen-binding fragment of the invention.

As described, in one embodiment, the invention is an antibody or antigen-binding fragment that binds to a complementary peptide, wherein the complementary peptide is encoded by the complement of a nucleotide sequence encoding thrombin or a portion thereof. In one embodiment, the antibody or antigen-binding fragment binds to a complementary peptide that is encoded by the complement of a nucleotide sequence encoding a thrombin. In another embodiment, the antibody or antigen-binding fragment binds to a complementary peptide that is encoded by the complement of a nucleotide sequence encoding a portion of thrombin. In one embodiment, the thrombin or portion thereof (which is encoded by the sense or +RNA strand and is the complement of the RNA strand encoding the complementary peptide to which the antibody or antigen-binding fragment binds) is a mammalian thrombin or a portion of a mammalian thrombin. In another embodiment, the thrombin or portion thereof is a human thrombin or a portion of a human thrombin.

In one embodiment, the antibody or antigen-binding fragment binds to a complementary peptide that is encoded by the complement of a nucleotide sequence encoding a portion of thrombin. In one embodiment, the portion of thrombin (which is encoded by the sense or +RNA strand and is the complement of the RNA strand encoding the complementary peptide to which the antibody or antigen-binding fragment binds) is a thrombin receptor binding domain or a portion thereof. As used herein, a thrombin receptor binding domain or a portion thereof is a segment of thrombin that is capable of selectively binding to the high-affinity non-proteolytically activated thrombin receptor (NPAR). Such thrombin receptor binding domains contain a domain (represented by residues 517-520 of human prothrombin) with a sequence homologous to the tripeptide cell binding domain of fibronectin, [Arg-Gly-Asp]. In a particular embodiment, the thrombin receptor binding domain or portion thereof has the amino acid sequence AGYKPDEGKRGDACEGDSGGPFV (i.e., amino acids 508-530 of human pro-thrombin (SEQ ID NO:1)). In another embodiment, the thrombin receptor binding domain or portion thereof is a portion of the thrombin receptor binding domain and has the amino acid sequence EGKRGDACEG (SEQ ID NO:2).

As described herein, complementary peptides of domains of thrombin that are encoded by both the 5'-3' sequence of the antisense RNA strand and the 3'-5' sequence of the antisense RNA strand can be used to produce the antibodies and antigen-binding domains of the invention. Therefore, in one embodiment, the complementary peptide (to which the antibodies and antigen-binding fragments of the invention bind) is encoded by the 5'-3' sequence of the antisense RNA strand. In another embodiment, the complementary peptide is encoded by the 3'-5' sequence of the antisense RNA strand.

In one embodiments, the complementary peptide (to which the antibodies and antigen-binding fragments of the invention bind) has the amino acid sequence KGSPTVTFTGIPCFPFIRLVTS (AC-23; SEQ ID NO:3). In another embodiment, the complementary peptide has the amino acid sequence KGSPTVTFTGIPSFPFIRLVTS (23C53; SEQ ID NO:4). In yet another embodiment, the complementary peptide has the amino acid sequence TFTGIPSFPF (C1053; SEQ ID NO:5). In still another embodiment, the complementary peptide has the amino acid sequence RPMFGLLPFAPLRTLPLSPPGKQ (AC-23rev, which is the complementary 5'-3' peptide corresponding to AC-23 (SEQ ID NO:6)). In still a further embodiment, the complementary peptide has the amino acid sequence LPFAPLRTLP (C1053rev, which is the complementary 5'-3' peptide corresponding to C1053 (SEQ ID NO:7)).

In one embodiment, the antibody or antigen-binding fragment of the invention is an agonist antibody or antigen-binding fragment thereof. In another embodiment, the antibody or antigen-binding fragment of the invention is an antagonist antibody or antigen-binding fragment thereof. Agonist antibodies and antigen-binding fragments thereof and antagonist antibodies and antigen-binding fragments thereof (and particular indications using such antibodies and antigen-binding fragments) are described in greater detail below.

In particular embodiments, the antibody or antigen-binding fragment is a polyclonal antibody, a monoclonal antibody or antigen-binding fragment thereof, a human antibody or antigen-binding fragment thereof, a humanized antibody or antigen-binding fragment thereof, or a chimeric antibody or antigen-binding fragment thereof. In one embodiment, the antibody or antigen-binding fragment is an antigen-binding fragment (e.g., an Fab fragment, an Fab' fragment, an F(ab')$_2$ fragment or an Fv fragment).

In one embodiment, the antibody or antigen-binding fragment thereof binds to a cysteine-altering complementary peptide having the amino acid sequence KGSPTVTFTGIPSFPFIRLVTS (23C53; SEQ ID NO:4). 23C53, which differs from AC-23 by a single amino acid, is the complementary peptide of TP508, except that it possesses a single amino acid alteration from Cys to Ser (see FIG. 4)

In one embodiment, the invention is a cell that produces an antibody or antigen-binding fragment thereof that binds to a complementary peptide encoded by the complement of a nucleotide sequence encoding a portion of thrombin. Suitable cells are described herein and are known in the art.

Antagonist and Agonist Antibodies and Antigen-Binding Fragments Thereof

As described herein and as known in the art, particular thrombin peptide fragments and derivatives can act as "thrombin receptor agonists" or "thrombin receptor antagonists". As used herein, a "thrombin receptor agonist" refers to a molecule that stimulates or activates the non-proteolytically activated thrombin receptor (NPAR) (Horvat, R., et. al., *J. Cell Sci.* 108:1155-64 (1995)). Compounds that stimulate NPAR are said to be NPAR agonists. NPAR is a high-affinity thrombin receptor present on the surface of most cells. This NPAR component is largely responsible for high-affinity binding of thrombin, proteolytically-inactivated thrombin, and thrombin-derived peptides to cells. NPAR appears to mediate a number of cellular signals that are initiated by thrombin independent of its proteolytic activity. An example of one such signal is the upregulation of annexin V and other molecules identified by subtractive hybridization (see Sower, et. al., *Experimental Cell Research* 247:422 (1999)). NPAR is therefore characterized by its high affinity interaction with thrombin at cell surfaces and its activation by proteolytically inactive derivatives of thrombin and thrombin-derived peptide agonists. NPAR activation can be assayed based on the ability of molecules to stimulate cell proliferation when added to fibroblasts in the presence of submitogenic concentrations of thrombin or molecules that activate protein kinase C (e.g., as described in U.S. Pat. Nos. 5,352,664 and 5,500,412). NPAR agonists can be identified by this activation or by their ability to compete with $^{125}$I-thrombin binding to cells.

In one embodiment, the antibody or antigen-binding fragment of the invention is an agonist antibody or antigen-binding fragment. As defined herein, an agonist antibody or antigen-binding fragment can both bind to, and stimulate, a thrombin receptor (e.g., the non-proteolytically activated thrombin receptor (NPAR)). Agonist antibodies to thrombin have been described in the art. For example, Frost et al. teach that a monoclonal antibody, TR-9, can mimic the effects of thrombin's high affinity interaction with the high affinity thrombin receptor (Frost, G. H., et al., *J. Cell Biol.* 105(6): 2551-58(1897)).

Similar to the agonist peptide derivatives described in U.S. Pat. No. 5,500,412, the agonist antibodies and antigen-binding fragments of the invention can be used to promote wound healing. In a particular embodiment, the agonist antibodies or antigen-binding fragments can be used to potentiate cell growth (either in vitro or in vivo).

In another embodiment, the antibody or antigen-binding fragment of the invention is an antagonist antibody. As defined herein, an antagonist antibody can bind to a thrombin receptor (e.g., the non-proteolytically activated thrombin receptor (NPAR)) and inhibit activation of this receptor by agonists, such as thrombin, TP508 and other agonist peptide derivatives (e.g., those described in U.S. Pat. Nos. 5,352,664 and 5,500,412).

As described herein, such antagonist antibodies and antigen-binding fragments can be used for a number of indications. For example, the antagonist antibodies and antigen-binding fragments of the invention can be used to inhibit scar tissue formation (e.g., scar formation in burn patients, scar formation in patients who have undergone opthalmic surgery, keloidal scar formation). The antagonist antibodies and antigen-binding fragments of the invention can also be used to inhibit the formation of tissue adhesions, defined as abnormal unions between body organs by formation of fibrous tissue. It is known that fibroblast proliferation is required for formation of such adhesions. Given that alpha-thrombin is known to induce fibroblast proliferation, it follows that inhibition of thrombin-mediated mitogenesis by the antagonist antibodies and antigen-binding fragments of the invention can reduce adhesion formation (e.g., adhesion formation following certain surgical procedures (e.g., adhesion formation following gynecologic or thoracic surgery)). The antagonist antibodies and antigen-binding fragments of the invention can further be used to inhibit tumor metastasis or angiogenesis. In one embodiment, the antagonist antibodies and antigen-binding fragments of the invention can be used to inhibit cell proliferation.

Methods of Screening

As described herein, in addition to having known protease-activated receptors (e.g., PAR-1, PAR-2, PAR-3 and PAR-4), thrombin is also able to promote growth of a wide variety of cell types through activation of a specific uncloned cell surface receptor known as the non-proteolytically activated thrombin receptor (NPAR) (Horvat, R., et. al., *J. Cell Sci.* 108, 1155-64 (1995)). The antibodies and antigen-binding fragments of the invention, because they bind particular complementary peptides of thrombin, may also bind NPAR. Such antibodies and antigen-binding fragments can thus be used to detect NPAR. Therefore, in one embodiment, the invention is a method of detecting NPAR comprising:

a) contacting a sample (e.g., cells expressing NPAR) with an antibody or antigen-binding of the invention, under conditions suitable for binding of the antibody or antigen-binding fragment to NPAR present in the sample; and
b) detecting antibody-NPAR complexes or antigen-binding fragment-NPAR complexes, wherein detection of said antibody-NPAR complexes or antigen-binding fragment-NPAR complexes is indicative of the presence of NPAR in said sample. In a particular embodiment, the antibody or antigen-binding fragment comprises a detectable label. Suitable labels include, but are not limited to, those described herein (e.g., a radioisotope, an epitope label (tag), an affinity label (e.g., biotin, avidin), a spin label, an enzyme, a fluorescent group or a chemiluminescent group).

In addition, because the antibodies and antigen-binding fragments of the invention bind particular complementary peptides of thrombin (and therefore may bind NPAR), they can be used to detect or identify agents that bind to NPAR. In one embodiment, the invention is a method of detecting and/or identifying an agent that binds to NPAR comprising combining:

i) an antibody or antigen-binding fragment of the invention;
ii) a test agent; and
iii) a composition comprising NPAR;

and detecting or measuring the formation of a complex between the antibody or antigen-binding fragment and NPAR, wherein a decrease in the formation of said complex relative to a suitable control (e.g., absence of the test agent) indicates that the test agent binds to NPAR.

Production of antibodies and antigen-binding fragments that can bind NPAR also allow for identification, characterization, cloning and sequencing of NPAR. Given the importance of NPAR in promoting the growth of a wide variety of cell types, it would be beneficial to molecularly characterize this receptor. The antibodies and antigen-binding fragments of the invention can allow for such identification, purification and isolation. For example, antibodies and antigen-binding fragments that bind NPAR could be used to purify and isolate the receptor. Such isolation would allow one skilled in the art to deduce the amino acid sequence of NPAR or a portion of NPAR (e.g., using Edman degradation). Using degenerate oligonucleotide primers based on the determined amino acid sequence of NPAR or a portion of NPAR, one could use PCR to amplify a segment of genomic DNA encoding NPAR using cells that expresses NPAR. It would then be possible to screen a library (made from a cell type that expresses NPAR) to identify and isolate a full length clone encoding NPAR.

Methods of Treatment

As described, in particular embodiments, the antibody or antigen-binding fragment of the invention is either an agonist antibody or antigen-binding fragment thereof or an antagonist antibody or antigen-binding fragment thereof. Because thrombin is involved in a number of bioregulatory effects, both the agonist and antagonist antibodies and antigen-binding fragments of the invention have a number of clinical applications. As described in greater detail below, subjects in need can be treated with either agonist antibodies or antigen-binding fragments thereof, or antagonist antibodies or antigen-binding fragments thereof. A "subject", "individual" or "patient" is preferably a human, but can also be an animal in need of treatment with an antibody or antigen-binding fragment of the invention, e.g., companion animals (e.g., dogs, cats, and the like), farm animals (e.g., cows, pigs, horses and the like) and laboratory animals (e.g., rats, mice, guinea pigs and the like).

In particular embodiments, an effective amount of an antibody or antigen-binding fragment of the invention is administered to a subject in need thereof. An "effective amount" is the quantity of antibody or antigen-binding fragment (e.g., an agonist antibody or antigen-binding fragment thereof, an antagonist antibody or antigen-binding fragment thereof) that results in an improved clinical outcome of the condition being treated with the antibody or antigen-binding fragment compared with the absence of treatment. The amount of antibody or antigen-binding fragment administered will depend on the degree, severity, and type of the disease or condition, the amount of therapy desired, and the release characteristics of the pharmaceutical formulation. It will also depend on the subject's health, size, weight, age, sex and tolerance to drugs. Typically, the antibody or antigen-binding fragment is administered for a sufficient period of time to achieve the desired therapeutic effect.

Methods of Treatment Using Agonist Antibodies and Antigen-Binding Fragments

In particular embodiments, the invention is an agonist antibody or antigen-binding fragment thereof. Similar to the agonist peptide derivatives described in U.S. Pat. Nos. 5,500,412 and 5,352,664, the agonist antibodies and antigen-binding fragments of the invention can be used for a number of indications. For example, in one embodiment, the agonist antibodies or antigen-binding fragments are used to potentiate cell growth (either in vitro or in vivo). This method encompasses, but is not limited to, situations wherein one wishes to potentiate cell growth in vitro. Such cell-stimulatory uses may be potentiated by further providing an effective amount of alpha-thrombin (0.1 μg/ml-10 μg/ml), gamma-thrombin (0.1 μg/ml-10 μg/ml) or phorbol myristate acetate (10 ng/ml-100 ng/ml) in conjunction with the agonist antibody or antigen-binding fragment.

In another embodiment, the invention is a method for activating the non-proteolytically activated thrombin receptor (NPAR) in a subject in need of such treatment. These methods comprises the step of administering an effective amount of an agonist antibody or antigen-binding fragment of the invention.

Subjects "in need of treatment" with an agonist antibody or antigen-binding fragment of the invention are subjects with diseases and/or conditions that can be treated with agonist antibodies or antigen-binding fragments to achieve a beneficial therapeutic and/or prophylactic result. A beneficial outcome includes a decrease in the severity of symptoms or delay in the onset of symptoms, increased longevity and/or more rapid or more complete resolution of the disease or condition. For example, a subject in need of treatment can require cell proliferation involving chondrocytes, angiogenesis, bone growth, cardiac repair, wound healing, cartilage growth or repair, or inhibition of restenosis.

Thrombin peptide derivatives have been shown to stimulate proliferation of endothelial cells, fibroblasts, and keratinocytes (see, e.g., U.S. Pat. Nos. 5,500,412 and 5,352,664, the contents of which are incorporated herein by reference in their entirety). Accordingly, the agonist antibodies and antigen-binding fragments of the invention can similarly stimulate proliferation of such cells. Thus, in one embodiment, the agonist antibodies and antigen-binding fragments of the invention are used to promote wound healing (e.g., healing of acute wounds, such as, for example, burns, dermal wounds, surgical wounds and bone fractures). In addition, thrombin peptide derivatives have recently been shown to be particularly effective in promoting the healing of chronic wounds, such as, diabetic ulcers, venous ulcers, and pressure sores (see, e.g., WO 03/013569, the contents of which are incorporated herein by reference in their entirety). Accordingly, the agonist antibodies and antigen-binding fragments of the invention can similarly promote the healing of such chronic wounds.

Thrombin peptide derivatives have also been shown to stimulate cartilage growth or repair and the growth of chondrocytes (see, e.g., WO 02/07748, the contents of which are incorporated herein by reference in their entirety). Accordingly, the agonist antibodies and antigen-binding fragments of the invention can similarly stimulate cartilage growth or repair and the growth of chondrocytes. Thus, in one embodiment, the agonist antibodies and antigen-binding fragments of the invention are administered to stimulate cartilage growth or repair or chondrocyte growth and repair in, for example, patients with osteoarthritis or joint injuries. Other uses for the agonist antibodies and antigen-binding fragments of the invention include stimulating bone growth to promote healing of simple fractures, non-union fractures, voids and gaps in bone and bone grafts, preventing restenosis in patients after angioplasty and promoting the regeneration of blood vessels in cardiac tissue (see, e.g., WO 02/005836, WO 02/004008, and U.S. Patent Application Publication No. 2002/0128202, the contents of each of which are incorporated herein by reference in their entirety).

Induced bone growth can also be therapeutically beneficial at certain sites within a subject (referred to as "ectopic" sites) where bone tissue would not normally be found, such as a site in need of a bone graft or bone fusion. Fusions are commonly used to treat lower back pain by physically coupling one or more vertebrae to its neighbor. The bone created by such a fusion is located at a site not normally occupied by bone tissue. Induced bone growth at these ectopic sites can act as a "graft substitute" whereby induced bone growth between the vertebrae takes the place of a graft and obviates the need for a second operation to harvest bone for the grafting procedure. Induction of bone growth is also needed for treating acquired and congenital craniofacial and other skeletal or dental anomalies (see e.g., Glowacki et al., *Lancet* 1: 959 (1981)); performing dental and periodontal reconstructions where lost bone replacement or bone augmentation is required, such as in a jaw bone; and supplementing alveolar bone loss resulting from periodontal disease to delay or prevent tooth loss (see e.g., Sigurdsson et al., *J. Periodontol.*, 66: 511 (1995)). The agonist antibodies and antigen-binding fragments of the invention can therefore be used in such treatments as described above.

As described above, an "effective amount" is the quantity of antibody or antigen-binding fragment (e.g., an agonist antibody or antigen-binding fragment) that results in an improved clinical outcome of the condition being treated with the antibody or antigen-binding fragment compared with the absence of treatment. While this quantity can vary depending on a number of factors (e.g., as described above), for the indication of cardiac repair, typically between about 0.1 μM to 10 μM or more typically between about 50 to 250 μg per single injection of the agonist antibody or antigen-binding fragment is administered to a damaged tissue for a satisfactory increase in the rate of repair. For the indication of cartilage growth or repair, typically between about 0.1 μg per single application and about 1 mg per single application of the agonist antibody or antigen-binding fragment, preferably between about 25 μg and about 100 μg per 20 cubic mm, is administered. For the treatment of chronic dermal ulcer, typically between about 0.1 μg and about 1 mg per single application, preferably between about 1 μg and about 100 μg per single application, of the agonist antibody or antigen-binding fragment is administered. Particularly, one to seven applications per week of the agonist antibody or antigen-binding fragment is administered for the treatment of chronic dermal ulcer. For the indication of bone growth, typically between about 1 μg and about 1 mg per day, preferably between about 5 μg and about 100 μg per day, of the agonist antibody or antigen-binding fragment is administered.

Methods of Treatment Using Antagonist Antibodies and Antigen-Binding Fragments

In particular embodiments, the invention is an antagonist antibody or antigen-binding fragment thereof. Similar to the antagonist peptide derivatives described in U.S. Pat. Nos. 5,500,412 and 5,352,664, the antagonist antibodies and antigen-binding fragments of the invention can be used for a number of indications (e.g., inhibiting scar tissue formation, inhibiting formation of tissue adhesions, inhibiting tumor growth and metastasis, inhibiting cell proliferation).

For example, in one embodiment, the invention is a method of inhibiting scar tissue formation by administering to a wound or scar tissue, a therapeutically effective amount of an antagonist antibody or antigen-binding fragment of the invention. Typically, a concentration of the antagonist antibody or antigen-binding fragment is adequate when it is sufficient to inhibit thrombin receptor-mediated events. In a particular embodiment, an effective amount of the antagonist antibody or antigen-binding fragment is from about 1 ng/cm$^2$ to about 10 µg/cm$^2$ of wound surface. In general, such a method may be used in any situation in which scar formation is undesirable (e.g., on burn patients, on patients subjected to opthalmic surgery). Moreover, the methods may also be used to prevent keloidal scar formation. It is anticipated that spraying the wound with an aerosol spray will be a particularly sterile and efficacious manner of administering the antagonist antibody or antigen-binding fragment to the wounds of burn patients.

The antagonist antibodies and antigen-binding fragments can also be used to inhibit the formation of tissue adhesions. Tissue adhesions are abnormal unions between body organs by formation of fibrous tissue. It is known that fibroblast proliferation is required for formation of such adhesions. Given that alpha-thrombin is known to induce fibroblast proliferation, it follows that inhibition of thrombin-mediated mitogenesis by the antagonist antibodies and antigen-binding fragments of the invention can reduce adhesion formation. It is believed that administration of such antagonist antibodies and antigen-binding fragments to the surface of the affected organs will prove to be especially useful following certain surgical procedures, such as thoracic and gynecologic surgeries, where adhesions often lead to postoperative complications.

In another embodiment, the invention is a method of inhibiting tumor metastasis or angiogenesis in a subject comprising administering an antagonist antibody or antigen-binding fragment of the invention. As described in U.S. Pat. Nos. 5,500,412 and 5,352,664, such a method is supported by studies demonstrating that alpha-thrombin is able to disrupt normal inter-endothelial cell contacts that are important in preventing metastasis, as well as studies demonstrating that alpha-thrombin can induce the proliferation of endothelial cells required for angiogenesis. Accordingly, the invention provides a method whereby a subject (e.g., a mammal (e.g., a human)) with one or more tumors receives a therapeutically effective amount of an antagonist antibody or antigen-binding fragment of the invention. While exact doses would need to be determined by empirical methods known those of skill in the art, it is estimated that an amount sufficient to achieve a concentration of from about 0.1 µM to about 10 µM at the site to be treated is needed. It is contemplated that the antagonist antibodies and antigen-binding fragments will be most efficacious in this regard when administered intravenously. However, other methods of administration will also likely prove to be effective.

In a general embodiment, the invention provides for the use of antagonist antibodies and antigen-binding fragments to inhibit cell proliferation. This method encompasses, but is not limited to, situations in which one desires to inhibit cell proliferation in vitro. Of course, the antagonist antibodies and antigen-binding fragments can also be used as a general inhibitor of cell proliferation (e.g., in an in vivo context).

Pharmaceutical Compositions Comprising Antibodies or Antigen-Binding Fragments

In one embodiment, the invention is a pharmaceutical composition comprising an antibody or antigen-binding fragment of the invention and a pharmaceutically-acceptable carrier. Suitable pharmaceutical carriers may contain inert ingredients which do not inhibit the biological activity of the antibody or antigen-binding fragment. The carriers should be biocompatible, i.e., non-toxic, non-inflammatory, non-immunogenic and devoid of other undesired reactions at the administration site. Pharmaceutically-acceptable carriers vary according to the route of administration selected and the indication being treated. Examples of pharmaceutically-acceptable carriers include, for example, saline, aerosols, commercially available inert gels, or liquids supplemented with albumin, methylcellulose or a collagen matrix. Standard pharmaceutical formulation techniques can be employed, such as those described in Remington's Pharmaceutical Sciences, Mack Publishing Company, Easton, Pa.

The compositions of the present invention can be solutions, suspensions, emulsions, syrups, gels, ointments, lotions, creams, pastes, putty, extrusions, microparticles, capsules, tablets or the like.

A gel formulation is commonly used when the antibody or antigen-binding fragment (e.g., an agonist antibody, an agonist antigen-binding fragment) is being used to promote cardiac repair and wound healing. Gels are comprised of a base selected from an oleaginous base, water, or an emulsion-suspension base. The oleaginous base contains fixed oils or hydrocarbons, such as white petrolatum or mineral oil, or an absorbent base, e.g., consisting of an absorbent anhydrous substance or substances, for example, anhydrous lanolin. The emulsion-suspension base comprises an oil phase (internal phase) containing typically fixed oils, hydrocarbons, and the like, such as waxes, petrolatum, mineral oil, and the like, and an aqueous phase (continuous phase) comprising water and any water-soluble substances such as added salts. The two phases are stabilized by use of an emulsifying agent, for example, a surface active agent such as sodium lauryl sulfate, hydrophilic colloids, such as acacia colloidal clays, beegum, and the like. To the base is added a gelling agent which forms a matrix in the base, increasing its viscosity to a semisolid consistency. Examples of suitable gelling agents include hydroxypropyl cellulose, acrylic acid polymers, polymers of poly(ethylene oxide) or copolymers of ethylene and propylene oxide (see Cao et al., *J. Biomater. Sci* 9:475 (1998) and Sims et al., *Plast Reconstr. Surg.* 98:843 (1996); the entire teachings of both of which are incorporated herein by reference). Pluronic gels are nontoxic block copolymers of ethylene oxide and propylene oxide. They exhibit thermosetting properties that allow them to exist as viscous liquids at room temperature, but as gels at body temperatures. The active ingredients are added to the formulation at the desired concentration at a point preceding addition of the gelling agent or can be mixed after the gelation process. Gels for the treatment of promoting wound healing may be administered in a local topical administration.

Formulations for a local topical administration other than gels include ointments and creams. Ointments are typically prepared using the oleaginous base described previously. Creams generally comprise the emulsion-suspension base described previously. Following the formation of the base, the active ingredients are added in the desired concentration.

In another preferred embodiment, the disclosed pharmaceutical compositions are lyophilized pellets which can be reconstituted prior to use. The lyophilized pellets are commonly used for indications such as bone growth and cardiac repair. The lyophilized compositions optionally comprise a bulking agent in addition to the other active ingredients described previously. Suitable bulking agents include mannitol, lactose, cellulose, sorbitol, dextrose, dextran, polydextrose, maltitol, xylitol, isomalt, erythritol, glycerol and the like. The lyophilized compositions can be reconstituted to form solutions, and may contain auxiliary substances such as wetting or emulsifying agents, pH buffering agents, viscosity enhancing additives, preservatives and the like, depending upon the route of administration and the preparation desired.

The pharmaceutical compositions of the present invention can also be sustained release formulations for particular indications, such as bone growth, cartilage growth or repair and cardiac repair. The sustained release formulations can provide for continuous release of the antibody or antigen-binding fragment over a period of hours. Polymers are often used to form the sustained release formulations. Examples of the polymers include poly α-hydroxy esters, such as polylactic acid/polyglycolic acid (PLGA) homopolymers and copolymers, polyphosphazenes (PPHOS), polyanhydrides and poly (propylene fumarates) (PPF).

Polylactic acid/polyglycolic acid (PLGA) homo and copolymers are well known in the art as sustained release vehicles. The rate of release can be adjusted by the skilled artisan by variation of polylactic acid to polyglycolic acid ratio and the molecular weight of the polymer (see Anderson, et al., *Adv. Drug Deliv. Rev.* 28:5 (1997), the entire teachings of which are incorporated herein by reference). The incorporation of poly(ethylene glycol) into the polymer as a blend to form microparticle carriers allows further alteration of the release profile of the active ingredient (see Cleek et al., *J. Control Release* 48.259 (1997), the entire teachings of which are incorporated herein by reference). Ceramics, such as calcium phosphate and hydroxyapatite, can also be incorporated into the formulation to improve mechanical qualities. PLGA microparticles can also be mixed with pluronic gels or collagen to prevent aggregation and to make the microparticles suitable for direct injection. Preparation of PLGA microspheres of TP508 is described in detail in WO 03/061690, the contents of which are incorporated herein by reference in their entirety.

Degradation and drug release by PPHOS can be controlled by varying the amount of hydrolytically unstable side groups. With greater incorporation of either imidazolyl or ethylglycol substituted PPHOS, for example, an increase in degradation rate is observed (see Laurencin et al., *J Biomed Mater. Res.* 27:963 (1993), the entire teachings of which are incorporated herein by reference), thereby increasing the rate of drug release.

Polyanhydrides have well defined degradation and release characteristics that can be controlled by including varying amounts of hydrophobic or hydrophilic monomers, such as sebacic acid and 1,3-bis(p-carboxyphenoxy)propane (see Leong et al., *J. Biomed Mater. Res.* 19:941 (1985), the entire teachings of which are incorporated herein by reference). To improve mechanical strength, anhydrides are often copolymerized with imides to form polyanhydride-co-imides. Examples of polyanhydride-co-imides that are suitable for orthopaedic applications are poly(trimellitylimido-glycine-co-1,6-bis(carboxyphenoxy)hexane and pyromellityimidoalanine: 1,6-bis(p-carboxyphenoxy)hexane copolymers.

The pharmaceutical compositions of the instant invention can be administered by any suitable route, locally or systemically. Typically, the route of administration depends on the type of formulation being used and the indication treated. Topical administration is commonly used for treating wounds (e.g., using an agonist antibody or agonist antigen-binding fragment). For the topical administration, the pharmaceutical compositions are typically creams, gels, ointments or aerosols, as described previously in detail. For certain indications, such as stimulating bone growth, cartilage repair or growth and cardiac repair, it is advantageous to inject or implant the pharmaceutical composition of the instant invention directly in the treatment site.

For particular indications (e.g., cardiac repair, cartilage growth or repair, bone growth), the pharmaceutical compositions of the invention are typically injectable forms. For example, the disclosed injectable compositions can be injected directly at the site in need of bone growth and can conveniently be used to fill voids and fuse bones without the need for invasive surgery. "Injectable" means that the material can be injected by syringe through a standard needle used for injecting solutions, pastes or gels. The injectable compositions may be administered intravenously or directly at the site in need of treatment. The injectable compositions may further include physiological saline, bacteriostatic saline (saline containing about 0.9% mg/mL benzyl alcohol), phosphate-buffered saline, Hank's solution, Ringer's-lactate, or liquids supplemented with albumin, methyl cellulose, or hyaluronic acid. The injectable compositions may also include polymers of poly(ethylene oxide) or copolymers of ethylene and propylene oxide. Pluronic gels are examples of such polymers, and exhibit thermosetting property that allows them to exist as viscous liquids at room temperature, but as gels at body temperature, as discussed previously. Other compositions for the injectable delivery compositions include solutions of poly(propylene fumarate) (PPF) copolymers and pastes of calcium phosphate ceramics (see Schmitz et al., *J. Oral Maxillofacial Surgery* 57:1122 (1999), the entire teachings of which are incorporated herein by reference).

Implantable pharmaceutical compositions (e.g., pharmaceutical compositions containing an agonist antibody or antigen-binding fragment) are beneficial especially for indications such as stimulating bone growth, cartilage growth or repair and cardiac repair. "Implantation" or "administration at a site" means in sufficient proximity to the site in need of treatment so that the desired healing occurs (e.g., an improved clinical outcome of the condition being treated in the presence of the drug compared with its absence) at the site when the antibody or antigen-binding fragment is released from the pharmaceutical composition. It is understood that an implantable pharmaceutical composition may also be a sustained release formulation or an injectable formulation. For example, implantable pharmaceutical compositions can also comprise a sustained release carrier to achieve slow and continuous medications at the implantation site.

The implantable pharmaceutical compositions can be shaped as desired in anticipation of surgery or shaped by the physician or technician during surgery. It is preferred to shape the matrix to span a tissue defect and to take the desired form of the new tissue. In the case of bone repair of a non-union defect, for example, it is desirable to use dimensions that span the non-union. In bone formation procedures, the material is slowly absorbed by the body and is replaced by bone in the shape of or very nearly the shape of the implant.

Alternatively, the implantable pharmaceutical composition can be partially enclosed in a supporting physical structure such as a mesh, wire matrix, stainless steel cage, threaded interbody fusion cage and the like before administering to the site, for example, in need of bone growth.

In yet another alternative, the disclosed pharmaceutical compositions (e.g., pharmaceutical compositions comprising an agonist antibody or antigen-binding fragment for stimulating bone growth and cartilage repair or growth) advantageously comprise carriers that include porous matrices that can then serve as a scaffolding for bone and tissue growth onto which bone progenitor cells and osteogenic cells may migrate and attach. Such carriers are said to be osteoconductive. For certain applications, the carrier should have sufficient mechanical strength to maintain its three dimensional structure and help support the immobilization of the bone or tissue segments being united or grafted together. Examples of suitable osteoconductive carriers include collagen (e.g., bovine collagen), fibrin, calcium phosphate ceramics (e.g., hydroxyapatite and tricalcium phosphate), calcium sulfate, guanidine-extracted allogenic bone and combinations thereof. A number of suitable carriers are commercially available, such as COLLAGRAFT® (Cohension Technologies, Inc., Palo Alto, Calif.), which is a mixture of hydroxyapatite, tricalcium phosphate and fibrillar collagen, and PRO OSTEON 500™ (Interpore Cross International, Irvine, Calif.), which is a hydroxyapatite biomatrix formed by the conversion of marine coral calcium carbonate to crystalline hydroxyapatite. Descriptions of synthetic biodegradable polymers that can serve as osteoconductive carriers with sustained release characteristics can be found in Behravesh et al., *Clinical Orthopaedics* 367:S118 (1999) and Lichun et al., *Polymeric Delivery Vehicles for Bone Growth Factors* in "Controlled Drug Delivery—Designing Technologies for the Future" Park and Mrsny eds., American Chemical Society, Washington, D.C. (2000) (the entire teachings of both of which are incorporated herein by reference). Examples of the biodegradable polymers include poly α-hydroxy esters, such as polylactic acid/polyglycolic acid homopolymers and copolymers, polyphosphazenes (PPHOS), polyanhydrides and poly(propylene fumarates), which are described above.

Alternatively, the pharmaceutical compositions can be implanted at the site in the form of microparticles or microspheres. For example, the microparticles are placed in contact or in close proximity to the site in need of cardiac repair, bone growth, or cartilage repair either by surgically exposing the site and applying the microparticles on, or in close proximity to, the site by painting, pipetting, spraying, injecting or the like. Microparticles can also be delivered to the site by endoscopy or by laparoscopy. Poly(propylene fumarates) (PPF) are highly desirable biocompatible implantable carriers for use in repairing bone defects because they are an injectable, in situ polymerizable, biodegradable material. PPF, combined with a vinyl monomer (N-vinyl pyrrolidinone) and an initiator (benzoyl peroxide), forms an injectable solution that can be polymerized in situ. It is particularly suited for filling skeletal defects of a wide variety of sizes and shapes (see Suggs et al., *Macromolecules* 30:4318 (1997), Peter et al., *J. Biomater. Sci. Poly,. Ed.* 10:363 (1999) and Yaszemski et al., *Tissue Eng.* 1:41 (1995), the entire teachings of each of which are incorporated herein by reference). The addition of solid phase components, such as β-tricalcium phosphate and sodium chloride, can improve the mechanical properties of PPF polymers (see Peter et al., *J. Biomed. Mater. Res.* 44:314 (1999); the entire teachings of which are incorporated herein by reference). Methods for encapsulating compositions (such as in a coating of hard gelatin or cyclodextran) are known in the art (Baker, et al., "Controlled Release of Biological Active Agents", John Wiley and Sons, 1986).

Diseases and conditions, treatable with the disclosed pharmaceutical composition comprising an antibody or antigen-binding fragment of the invention, for example, wounds and angioplasty, are often accompanied by symptoms and infirmities such as pain and infection. In certain instances it may be advantageous to co-administer one or more additional pharmacologically active agents along with the pharmaceutical composition of the instant invention to address such issues. For example, managing pain and inflammation may require co-administration with an analgesic or an anti-inflammatory agent. Managing infection may require co-administration with antimicrobial, antibiotic or disinfectant agents.

The present invention is illustrated by the following Examples, which are not intended to be limiting in any way. The relevant teachings of all publications cited herein that have not explicitly been incorporated herein by reference, are incorporated herein by reference in their entirety.

EXAMPLES

Example 1

Thrombin Binding to Complementary Peptides

Materials and Methods

Complementary peptides (CPs) (AC-23, 23C53, C1053 and ND1053) were coated onto individual wells of 96 well plates by incubating in a 10 µg/ml solution of peptide in carbonate buffer (pH 9.5) or in Phosphate Buffered Saline (PBS) overnight at room temperature. The amino acid sequences of particular complementary peptides are described below and are depicted in FIG. 4. In particular, the following CPs were generated:

```
AC-23                                         (SEQ ID NO: 3)
n-K G S P T V T F T G I P C F P F I R L V T S-c;

23C53                                         (SEQ ID NO: 4)
n-K G S P T V T F T G I P S F P F I R L V T S-c;

C1053    n-T F T G I P S F P F-c;             (SEQ ID NO: 5)
and

ND1053 n-A L T S V P S F A F-c.               (SEQ ID NO: 17)
```

AC-23, 23C53 and C1053 were derived from the thrombin receptor binding domain of human thrombin. While 23C53 and C1053 are CPs (of differing lengths) to the thrombin receptor binding domain of human thrombin, AC-23 is a CP to the thrombin receptor binding domain of human thrombin having a single amino acid alteration from Cys to Ser. ND 1053 was derived from the thrombin receptor binding domain of bovine thrombin.

Prior to use, the wells were covered with blocking solution containing 0.1% bovine serum albumin (BSA) to reduce non-specific binding. The plates were rinsed and stored at 4° C. until used. To perform the binding experiments, the peptide-coated ELISA plates were blocked with 200 µl per well of blocking buffer (0.1% BSA (w/v) in PBS) for 90 minutes at room temperature. The plates were subsequently rinsed two times with distilled water. Total and nonspecific (NS) binding was determined, respectively, by adding 100 µl per well of 125 ng/ml of biotinylated thrombin ([B]-thrombin) alone or containing 12.5 µg/ml of unlabeled thrombin for 90 minutes at room temperature. The plates were then rinsed four times with PBSTT (PBS+0.5% v/v Tween 20 (polyoxyethylene sorbitan monolaurate)), and 100 µl of Avidin-HRP antibody (Becton Dickinson) diluted to 1:1000 was added per well for 120 minutes at room temperature. The plates were subsequently rinsed four times with PBSTT, and 100 µl of Turbo TMB substrate (Pierce) was added for 30 minutes at room temperature. The reaction was stopped by adding 100 µl per well of 1 N $H_2SO_4$ and the plates were read immediately at 450 nm using a Spectra Max Plus plate reader (Molecular Device). The specific binding of [B]-thrombin to the coated wells was determined by subtracting non-specific binding from total binding.

Results

The 23-amino acid thrombin peptide, TP508, initiates a cascade of signals that are involved in tissue repair without the proteolytic activity required to activate previously cloned thrombin receptors, suggesting that this molecule activates a separate non-proteolytically activated thrombin receptor. To help identify the receptor molecule to which TP508 binds, we designed and synthesized peptides that are complementary to TP508 and/or complementary to regions within the TP508 molecule thought to interact with the thrombin receptor (FIGS. 1-4). Based on evidence that TP508 binds to a thrombin receptor (see, e.g., U.S. Pat. Nos. 5,500,412 and 5,352,664 and Glenn, K. C., et al., Pept. Res. 1 (2):65-73 (1988)), we tested whether thrombin could bind specifically to complementary peptides that were adsorbed to ELISA plates. Specific thrombin binding was determined using indicated concentrations of biotinylated thrombin alone and with a 100-fold excess of unlabeled thrombin (to define nonspecific binding).

Figure 5:
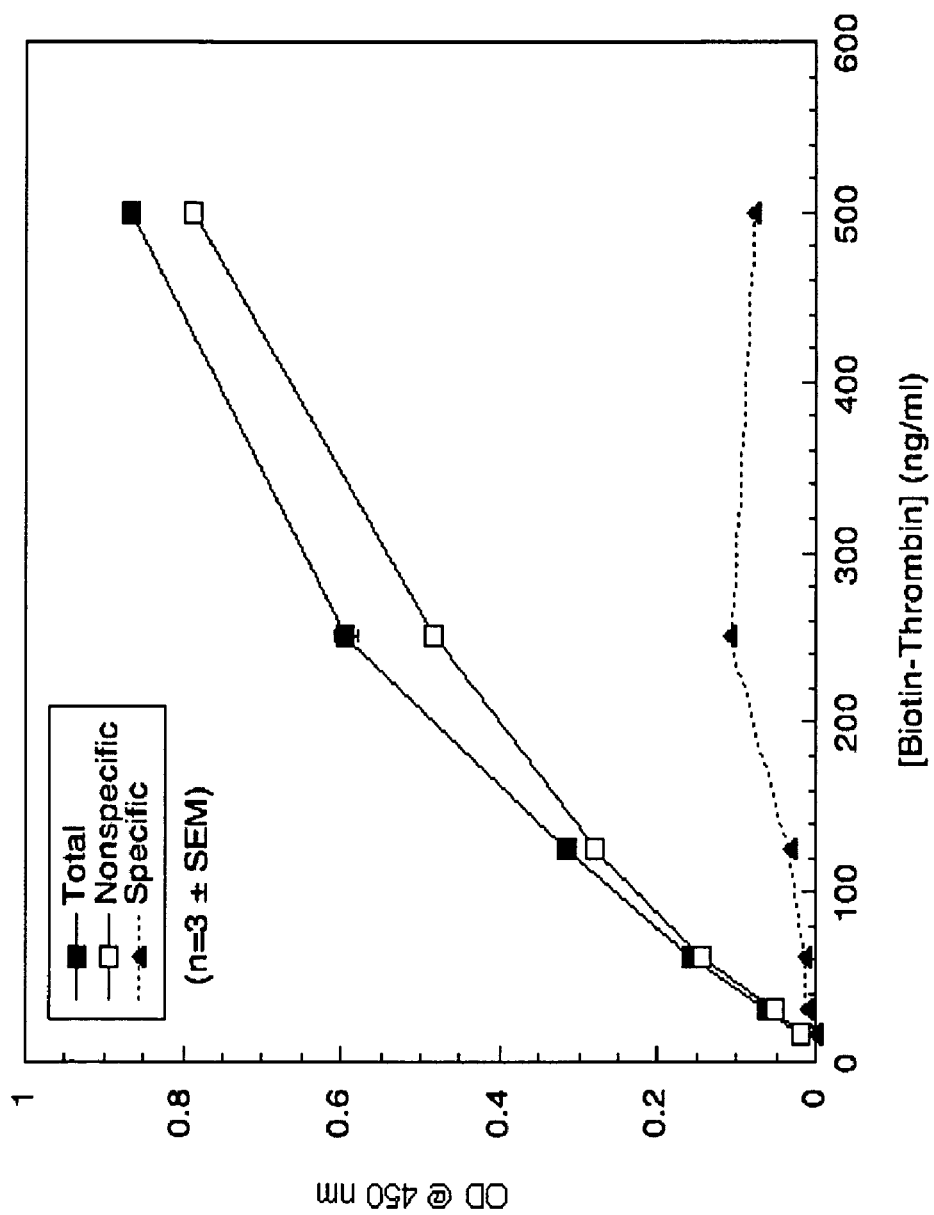
FIG. 5 is a graph showing binding of thrombin to the complementary peptide AC-23. AC-23-coated plates were incubated with biotinylated thrombin ("Total") or biotinylated thrombin plus a 40-fold excess of unlabeled thrombin ("Nonspecific") and binding was assayed using HRP-avidin. Specific binding ("Specific") of thrombin to AC-23 was determined by subtracting non-specific binding from total binding. Experiments were performed 3 times and results are indicated +/−SEM (standard error of the mean).
Figure 6:
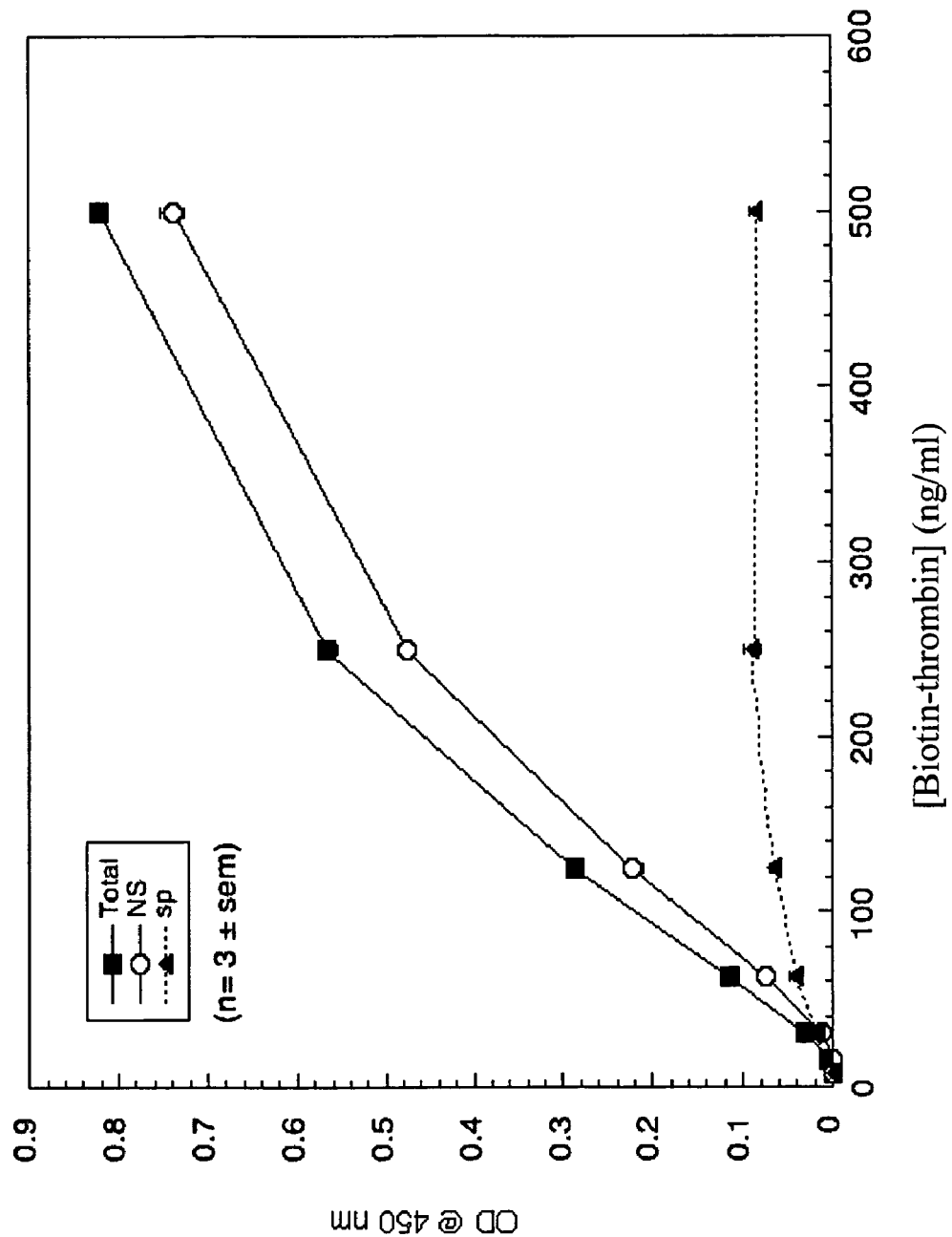
FIG. 6 is a graph showing binding of thrombin to the complementary peptide 23C53. 23C53-coated plated were incubated with biotinylated thrombin ("Total") or biotinylated thrombin plus a 40-fold excess of unlabeled thrombin ("NS") and binding was assayed using HRP-avidin. Specific binding ("sp") of thrombin to 23C53 was determined by subtracting non-specific binding from total binding. Experiments were performed 3 times and results are indicated +/−sem (standard error of the mean).

[B]-thrombin specifically bound to AC23 and 23C53 (see FIGS. 5 and 6) but not 10C53 (data not shown). In binding experiments in which increasing concentrations of [B]-thrombin were added, half maximal binding of [B]-thrombin to AC-23 was 4.8±0.2 nM (n=2±SD). Interestingly, this value is similar to that reported for high affinity thrombin binding to fibroblasts (Carney, D. H., and Cunningham, D. D., Cell 15(4):1341-49 (1978)).

Example 2

TP508 Inhibition of Binding of Thrombin to Complementary Peptides

Materials and Methods

Specific binding of [B]-thrombin (250 ng/ml) to wells coated with a complementary peptide (AC-23) was determined as described above. For the competition experiments, indicated concentrations of TP508 were added to the peptide-coated wells containing [B]-thrombin to determine if TP508 could compete for binding of [B]-thrombin to the CP.

Results

Figure 7:
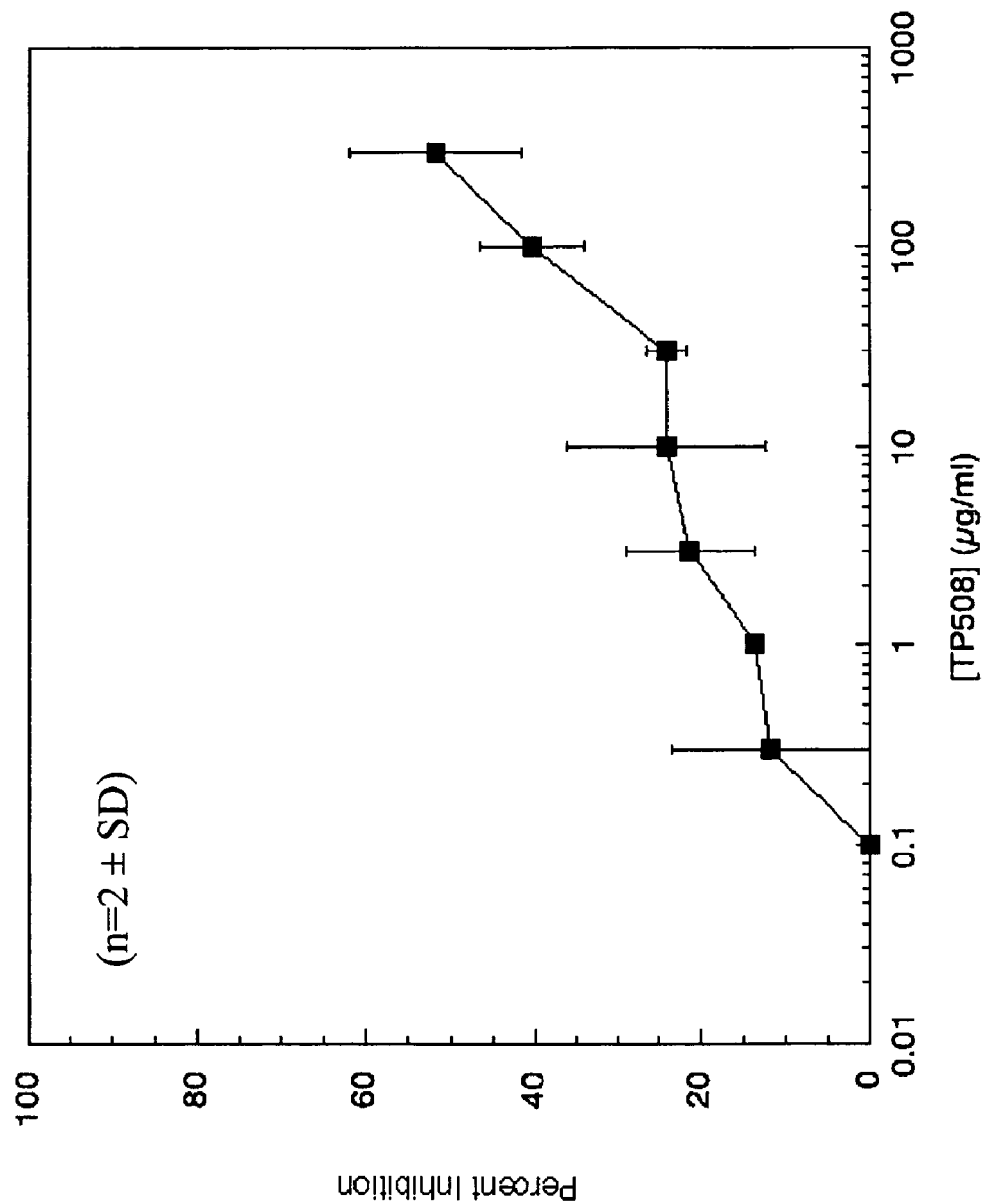
FIG. 7 is a graph showing inhibition of binding of thrombin to the complementary peptide AC-23 by the thrombin peptide derivative TP508 (H-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-NH$_2$; SEQ ID NO:1). AC-23-coated plated were incubated with biotinylated thrombin and indicated concentrations of TP508. The data demonstrate that up to 60% of the binding of thrombin to AC-23 can be inhibited by the addition of TP508. The experiment was performed twice and error bars represent ±SD.

As indicated in FIG. 7, addition of TP508 inhibited the specific binding of [B]-thrombin to AC-23. In particular, the results indicate that up to 60% of the binding of [B]-thrombin to the AC-23 can be inhibited by the addition of TP508 (FIG. 7). Therefore, both thrombin and TP508 bind to the complementary peptide, AC-23. This suggests that AC-23 has a three-dimensional structure that is similar to the thrombin-TP508 receptor on cells. Antibodies to AC-23 and other complementary peptides of thrombin can therefore be used to characterize the thrombin binding site that is activated by TP508, and can be used in the therapeutic and other methods described herein.

Example 3

Inhibition of Thrombin Binding to Membranes of B11-C Cells Using Antibodies to Complementary Peptides Materials and Methods
Generation of Polyclonal Antibodies Polyclonal antisera to the following complementary peptides were generated commercially by Sigma Genosis (The Woodlands, Tex.): AC-23 (SEQ ID NO:3); 23C53 (SEQ ID NO:4); C1053 (SEQ ID NO:5); AC-23rev (SEQ ID NO:6); and C1053rev (SEQ ID NO:7). In particular, AC-23, 23C53, 10C23, AC-23rev and C1053rev were synthesized and coupled at the N-terminal amino acid to keyhole limpet hemocyanin (KLH) using 1-Ethyl-3-(3-dimethylaminopropyl)carbodiimide-HCl. The peptide conjugate was then used to immunize New Zealand white rabbits to produce polyclonal sera using a standard immunization schedule. The immunization schedule was an initial immunization of 200 µg of the particular peptide conjugate in Complete Freund's Adjuvant followed by immunizations of 100 µg of the peptide conjugate in Incomplete Freund's Adjuvant administered 2, 4 and 6.5 weeks later. Serum was then obtained 7 days later. Additional immunizations with 100 µg of peptide conjugate in Incomplete Freund's Adjuvant were done every 2 weeks with serum collection (7 days after immunization) for another 3 months.

Preparation of Plasma Membranes

Plasma membranes were isolated from mouse B11-C cells by lysing the cells in hypotonic lysis buffer containing KCl, MgCl and Tris Buffer. Cells were then homogenized using a polytron and the homogenate was centrifuged at 10,000×g for 5 minutes at 4° C. The supernatants were subsequently centrifuged at 10,000×g for 20 minutes to remove cellular material. The supernatants of the 10,000×g centrifugation were then centrifuged at 125,000×g for 70 minutes, and the resulting membrane pellets were resuspended, aliquoted and frozen at −80° C. Membrane pellets were resuspended in tris-buffered saline and blotted onto nitrocellulose filters. The filters were incubated with 125 ng/ml of $^{125}$I-labeled thrombin (which was labeled as described in Carney, D. H., and Cunningham, D. D., Cell 15(4):1341-49 (1978)) alone or in the presence of a 100-fold excess of unlabeled thrombin to determine specific binding.

Results

Figure 8:
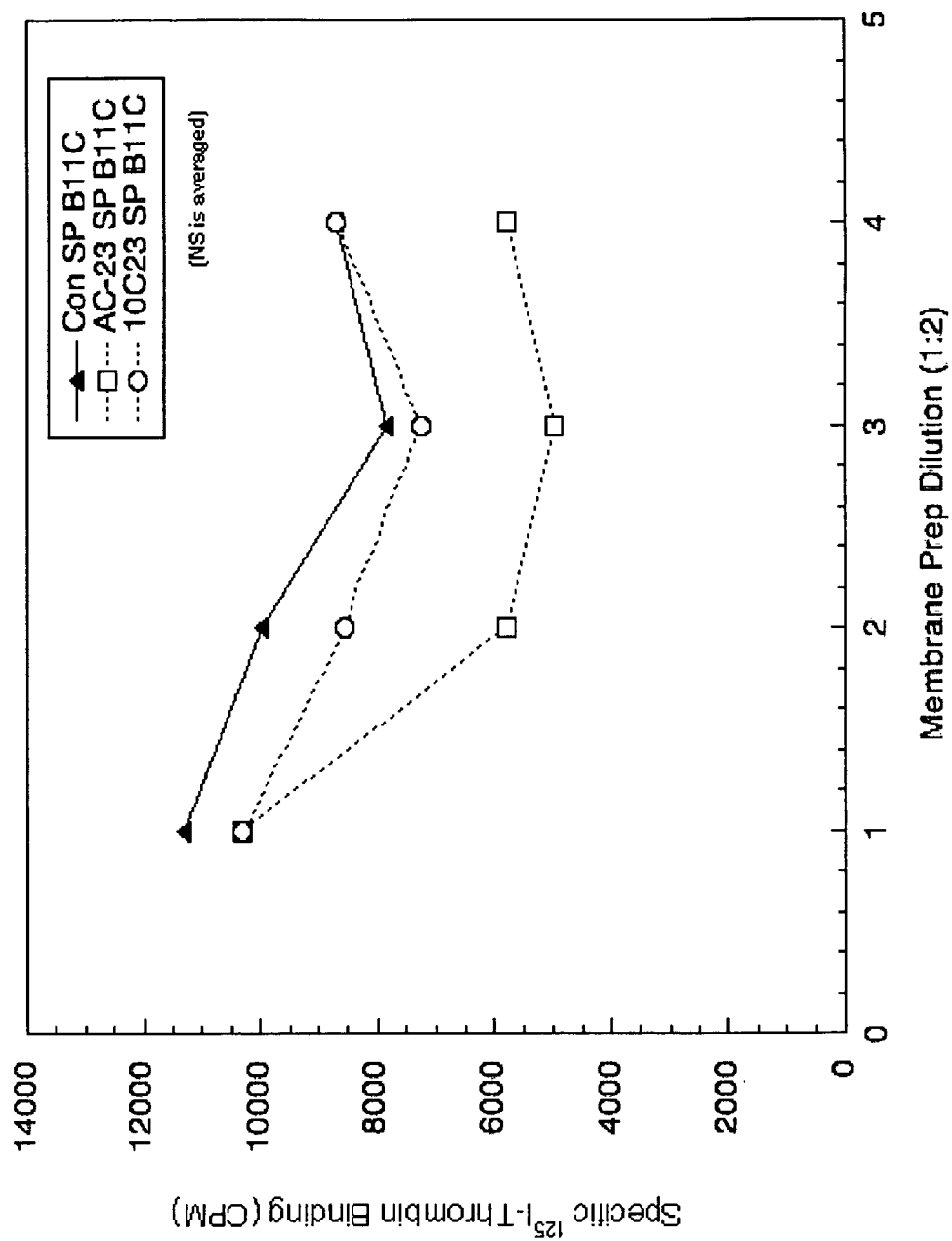
FIG. 8 is a graph depicting significant inhibition of binding of $^{125}$I-thrombin to plasma membranes from mouse B11-C cells by protein A-purified polyclonal antisera generated to AC-23 (324 µg/ml) but not polyclonal antisera generated to 10C23 (560 µg/ml). Plasma membrane preparations from mouse B11-C cells were blotted onto nitrocellulose filters and were incubated with $^{125}$I-thrombin and either polyclonal antisera generated to AC-23 or 10C23. Con SP B11C represents a control for specific binding, i.e., binding of thrombin to B11C cell membranes in the absence of any antibody.

As shown in FIG. 8, antibodies to AC23 (AC-23 SP B11C) but not antibodies to 10C23 (10C23 SP B11C) were able to significantly compete for at least part of the thrombin binding to the B11C cell membrane preparations. Given that thrombin has a number of binding sites, the failure of the antibodies to 10C23 to compete for binding of thrombin to the cell membranes is not unexpected. These results demonstrate that antibodies to AC-23 and other complementary peptides of thrombin can be used to bind, and therefore identify and characterize, the non-proteolytically activated thrombin receptor. In addition, such antibodies can be used in the therapeutic, diagnostic and screening methods described herein.

What is claimed is:

1. An antibody or antigen-binding fragment thereof that binds to a complementary peptide, wherein said complementary peptide is encoded by the complement of a nucleotide sequence encoding a portion of thrombin, wherein said portion of thrombin is a thrombin receptor binding domain or a portion thereof; and wherein said thrombin receptor binding domain or portion thereof is a thrombin receptor binding domain having the amino acid sequence AGYKPDEGKRGDACEGDSGGPFV (SEQ ID NO:1).

2. The antibody or antigen-binding fragment of claim 1, wherein said complementary peptide has the amino acid sequence KGSPTVTFTGIPCFPFIRLVTS (SEQ ID NO:3).

3. The antibody or antigen-binding fragment of claim 1, wherein said antibody or antigen-binding fragment is an agonist antibody or antigen-binding fragment thereof.

4. The antibody or antigen-binding fragment of claim 1, wherein said antibody or antigen-binding fragment is an antibody.

5. The antibody or antigen-binding fragment of claim 4, wherein said antibody is a polyclonal antibody.

6. The antibody or antigen-binding fragment of claim 1, wherein said antibody or antigen-binding fragment is a monoclonal antibody or an antigen-binding fragment thereof.

7. The antibody or antigen-binding fragment of claim 1, wherein said antibody or antigen-binding fragment is selected from the group consisting of a human antibody, a humanized antibody, a chimeric antibody and an antigen-binding fragment of any of the foregoing.

8. The antibody or antigen-binding fragment of claim 1, wherein said antibody or antigen-binding fragment is an antigen-binding fragment.

9. The antibody or antigen-binding fragment of claim 8, wherein said antigen-binding fragment is selected from the group consisting of an Fab fragment, an Fab' fragment, an $F(ab')_2$ fragment and an Fv fragment.

10. An isolated cell that produces an antibody or antigen-binding fragment thereof, wherein said antibody or antigen-binding fragment binds to a complementary peptide encoded by the complement of a nucleotide sequence encoding a portion of thrombin, wherein said portion of thrombin is a thrombin receptor binding domain or a portion thereof, and wherein said thrombin receptor binding domain or portion thereof is a thrombin receptor binding domain having the amino acid sequence AGYKPDEGKRGDACEGDSGGPFV (SEQ ID NO:1).

11. A pharmaceutical composition comprising an antibody or antigen-binding fragment thereof and a pharmaceutically-acceptable carrier, wherein said antibody or antigen-binding fragment binds to a complementary peptide encoded by the complement of a nucleotide sequence encoding a portion of thrombin, wherein said portion of thrombin is a thrombin receptor binding domain or a portion thereof, and wherein said thrombin receptor binding domain or portion thereof is a thrombin receptor binding domain having the amino acid sequence AGYKPDEGKRGDACEGDSGGPFV (SEQ ID NO:1).

* * * * *

SEQUENCE LISTING

<160> NUMBER OF SEQ ID NOS: 19

<210> SEQ ID NO 1
<211> LENGTH: 23
<212> TYPE: PRT
<213> ORGANISM: Homo sapiens

```
<400> SEQUENCE: 1

Ala Gly Tyr Lys Pro Asp Glu Gly Lys Arg Gly Asp Ala Cys Glu Gly
1               5                  10                  15

Asp Ser Gly Gly Pro Phe Val
            20

<210> SEQ ID NO 2
<211> LENGTH: 10
<212> TYPE: PRT
<213> ORGANISM: Homo sapiens

<400> SEQUENCE: 2

Glu Gly Lys Arg Gly Asp Ala Cys Glu Gly
1               5                  10

<210> SEQ ID NO 3
<211> LENGTH: 22
<212> TYPE: PRT
<213> ORGANISM: Artificial Sequence
<220> FEATURE:
<223> OTHER INFORMATION: complementary peptides

<400> SEQUENCE: 3

Lys Gly Ser Pro Thr Val Thr Phe Thr Gly Ile Pro Cys Phe Pro Phe
1               5                  10                  15

Ile Arg Leu Val Thr Ser
            20

<210> SEQ ID NO 4
<211> LENGTH: 22
<212> TYPE: PRT
<213> ORGANISM: Artificial Sequence
<220> FEATURE:
<223> OTHER INFORMATION: complementary peptides

<400> SEQUENCE: 4

Lys Gly Ser Pro Thr Val Thr Phe Thr Gly Ile Pro Ser Phe Pro Phe
1               5                  10                  15

Ile Arg Leu Val Thr Ser
            20

<210> SEQ ID NO 5
<211> LENGTH: 10
<212> TYPE: PRT
<213> ORGANISM: Artificial Sequence
<220> FEATURE:
<223> OTHER INFORMATION: complementary peptides

<400> SEQUENCE: 5

Thr Phe Thr Gly Ile Pro Ser Phe Pro Phe
1               5                  10

<210> SEQ ID NO 6
<211> LENGTH: 23
<212> TYPE: PRT
<213> ORGANISM: Artificial Sequence
<220> FEATURE:
<223> OTHER INFORMATION: complementary peptides

<400> SEQUENCE: 6

Arg Pro Met Phe Gly Leu Leu Pro Phe Ala Pro Leu Arg Thr Leu Pro
1               5                  10                  15

Leu Ser Pro Pro Gly Lys Gln
            20
```

```
<210> SEQ ID NO 7
<211> LENGTH: 10
<212> TYPE: PRT
<213> ORGANISM: Artificial Sequence
<220> FEATURE:
<223> OTHER INFORMATION: complementary peptides

<400> SEQUENCE: 7

Leu Pro Phe Ala Pro Leu Arg Thr Leu Pro
  1               5                  10

<210> SEQ ID NO 8
<211> LENGTH: 24
<212> TYPE: RNA
<213> ORGANISM: Artificial Sequence
<220> FEATURE:
<223> OTHER INFORMATION: example RNA

<400> SEQUENCE: 8
auggaacacu uccgcuggggg caag                                              24

<210> SEQ ID NO 9
<211> LENGTH: 24
<212> TYPE: RNA
<213> ORGANISM: Artificial Sequence
<220> FEATURE:
<223> OTHER INFORMATION: example RNA

<400> SEQUENCE: 9
cuugccccag cggaaguguu ccau                                               24

<210> SEQ ID NO 10
<211> LENGTH: 8
<212> TYPE: PRT
<213> ORGANISM: Artificial Sequence
<220> FEATURE:
<223> OTHER INFORMATION: example peptide

<400> SEQUENCE: 10

Met Glu His Phe Arg Trp Gly Lys
  1               5

<210> SEQ ID NO 11
<211> LENGTH: 8
<212> TYPE: PRT
<213> ORGANISM: Artificial Sequence
<220> FEATURE:
<223> OTHER INFORMATION: example peptide

<400> SEQUENCE: 11

Leu Ala Pro Ala Glu Val Phe His
  1               5

<210> SEQ ID NO 12
<211> LENGTH: 69
<212> TYPE: DNA
<213> ORGANISM: Homo sapiens

<400> SEQUENCE: 12
gctggttaca agcctgatga agggaaacga ggggatgcct gtgaaggtga cagtggggga      60
cccttttgtc                                                             69

<210> SEQ ID NO 13
<211> LENGTH: 69
<212> TYPE: DNA
<213> ORGANISM: Homo sapiens
```

<400> SEQUENCE: 13
cgaccaatgt tcggactact tcccttt gct cccctacgga cacttccact gtcacccct        60 gggaaacag                                                                69

<210> SEQ ID NO 14
<211> LENGTH: 23
<212> TYPE: PRT
<213> ORGANISM: Artificial Sequence
<220> FEATURE:
<223> OTHER INFORMATION: complementary peptide

<400> SEQUENCE: 14

Arg Pro Met Phe Gly Leu Leu Pro Phe Ala Pro Leu Arg Thr Leu Pro
1               5                   10                  15

Leu Ser Pro Pro Gly Lys Gln
            20

<210> SEQ ID NO 15
<211> LENGTH: 69
<212> TYPE: DNA
<213> ORGANISM: Artificial Sequence
<220> FEATURE:
<223> OTHER INFORMATION: antiparallel complement

<400> SEQUENCE: 15
gacaaagggt cccccactgt caccttcaca ggcatcccct gctttccctt catcaggctt        60
gtaaccagc                                                                69

<210> SEQ ID NO 16
<211> LENGTH: 23
<212> TYPE: PRT
<213> ORGANISM: Artificial Sequence
<220> FEATURE:
<223> OTHER INFORMATION: antiparallel complementary peptide

<400> SEQUENCE: 16

Asp Lys Gly Ser Pro Thr Val Thr Phe Thr Gly Ile Pro Cys Phe Pro
1               5                   10                  15

Phe Ile Arg Leu Val Thr Ser
            20

<210> SEQ ID NO 17
<211> LENGTH: 10
<212> TYPE: PRT
<213> ORGANISM: Artificial Sequence
<220> FEATURE:
<223> OTHER INFORMATION: complementary peptide

<400> SEQUENCE: 17

Ala Leu Thr Ser Val Pro Ser Phe Ala Phe
1               5                   10

<210> SEQ ID NO 18
<211> LENGTH: 1997
<212> TYPE: DNA
<213> ORGANISM: Homo sapiens

<400> SEQUENCE: 18
aattcctcag tgacccagga gctgacacac tatggcgcac gtccgaggct tgcagctgcc        60
tggctgcctg gccctggctg ccctgtgtag ccttgtgcac agccagcatg tgttcctggc       120
tcctcagcaa gcacggtcgc tgctccagcg ggtccggcga gccaacacct tcttggagga       180

```
ggtgcgcaag ggcaacctag agcgagagtg cgtggaggag acgtgcagct acgaggaggc    240
cttcggggct ctggagtcct ccacggctac ggatgtgttc tgggccaagt acacagcttg    300
tgagacagcg aggacgcctc gagataagct tgctgcatgt ctggaaggta actgtgctga    360
gggtctgggt acgaactacc gagggcatgt gaacatcacc cggtcaggca ttgagtgcca    420
gctatggagg agtcgctacc cacataagcc tgaaatcaac tccactaccc atcctggggc    480
cgacctacag gagaatttct gccgcaaccc cgacagcagc accacgggac cctggtgcta    540
cactacagac cccaccgtga ggaggcagga atgcagcatc cctgtctgtg ccaggatca     600 agtcactgta gcgatgactc cacgctccga aggctccagt gtgaatctgt cacctccatt    660
ggagcagtgt gtccctgatc ggggcagca gtaccagggg cgcctggcgg tgaccacaca    720
tgggctcccc tgcctggcct gggccagcgc acaggccaag ccctgagca agcaccagga     780 cttcaactca gctgtgcagc tggtggagaa cttctgccgc aacccagacg ggatgagga    840 gggcgtgtgg tgctatgtgg ccgggaagcc tggcgacttt gggtactgcg acctcaacta    900
ttgtgaggag gccgtggagg aggagacagg agatgggctg gatgaggact cagacagggc    960
catcgaaggc cgtaccgcca ccagtgagta ccagactttc ttcaatccga ggacctttgg    1020
ctcgggagag gcagactgtg ggctgcgacc tctgttcgag aagaagtcgc tggaggacaa    1080
aaccgaaaga gagctcctgg aatcctacat cgacgggcgc attgtggagg ctcggatgc     1140 agagatcggc atgtcacctt ggcaggtgat gcttttccgg aagagtcccc aggagctgct    1200
gtgtggggcc agcctcatca gtgaccgctg ggtcctcacc gccgcccact gcctcctgta    1260
cccgccctgg gacaagaact tcaccgagaa tgaccttctg gtgcgcattg gcaagcactc    1320
ccgcacaagg tacgagcgaa acattgaaaa gatatccatg ttggaaaaga tctacatcca    1380
ccccaggtac aactggcggg agaacctgga ccgggacatt gccctgatga agctgaagaa    1440
gcctgttgcc ttcagtgact acattcaccc tgtgtgtctg cccgacaggg agacggcagc    1500
cagcttgctc caggctggat acaaggggcg ggtgacaggc tggggcaacc tgaaggagac    1560
gtggacagcc aacgttggta aggggcagcc cagtgtcctg caggtggtga acctgcccat    1620
tgtggagcgg ccggtctgca aggactccac ccggatccgc atcactgaca catgttctg    1680 tgctggttac aagcctgatg aagggaaacg aggggatgcc tgtgaaggtg acagtggggg    1740
accctttgtc atgaagagcc cctttaacaa ccgctggtat caaatgggca tcgtctcatg    1800
gggtgaaggc tgtgaccggg atgggaaata tggcttctac acacatgtgt ccgcctgaa     1860 gaagtggata cagaaggtca ttgatcagtt tggagagtag gggccactca tattctgggc    1920
tcctggaacc aatcccgtga agaattatt tttgtgtttc taaaactatg gttcccaata    1980
aaagtgactc tcagcgg                                                  1997
```

```
<210> SEQ ID NO 19
<211> LENGTH: 622
<212> TYPE: PRT
<213> ORGANISM: Homo sapiens

<400> SEQUENCE: 19

Met Ala His Val Arg Gly Leu Gln Leu Pro Gly Cys Leu Ala Leu Ala
 1               5                  10                  15

Ala Leu Cys Ser Leu Val His Ser Gln His Val Phe Leu Ala Pro Gln
            20                  25                  30

Gln Ala Arg Ser Leu Leu Gln Arg Val Arg Arg Ala Asn Thr Phe Leu
        35                  40                  45

Glu Glu Val Arg Lys Gly Asn Leu Glu Arg Glu Cys Val Glu Glu Thr
```

```
            50                  55                  60
Cys Ser Tyr Glu Glu Ala Phe Gly Ala Leu Glu Ser Ser Thr Ala Thr
 65                  70                  75                  80

Asp Val Phe Trp Ala Lys Tyr Thr Ala Cys Glu Thr Ala Arg Thr Pro
                     85                  90                  95

Arg Asp Lys Leu Ala Ala Cys Leu Glu Gly Asn Cys Ala Glu Gly Leu
                100                 105                 110

Gly Thr Asn Tyr Arg Gly His Val Asn Ile Thr Arg Ser Gly Ile Glu
                115                 120                 125

Cys Gln Leu Trp Arg Ser Arg Tyr Pro His Lys Pro Glu Ile Asn Ser
                130                 135                 140

Thr Thr His Pro Gly Ala Asp Leu Gln Glu Asn Phe Cys Arg Asn Pro
145                 150                 155                 160

Asp Ser Ser Thr Thr Gly Pro Trp Cys Tyr Thr Thr Asp Pro Thr Val
                165                 170                 175

Arg Arg Gln Glu Cys Ser Ile Pro Val Cys Gly Gln Asp Gln Val Thr
                180                 185                 190

Val Ala Met Thr Pro Arg Ser Glu Gly Ser Ser Val Asn Leu Ser Pro
                195                 200                 205

Pro Leu Glu Gln Cys Val Pro Asp Arg Gly Gln Gln Tyr Gln Gly Arg
210                 215                 220

Leu Ala Val Thr Thr His Gly Leu Pro Cys Leu Ala Trp Ala Ser Ala
225                 230                 235                 240

Gln Ala Lys Ala Leu Ser Lys His Gln Asp Phe Asn Ser Ala Val Gln
                245                 250                 255

Leu Val Glu Asn Phe Cys Arg Asn Pro Asp Gly Asp Glu Glu Gly Val
                260                 265                 270

Trp Cys Tyr Val Ala Gly Lys Pro Gly Asp Phe Gly Tyr Cys Asp Leu
                275                 280                 285

Asn Tyr Cys Glu Glu Ala Val Glu Glu Glu Thr Gly Asp Gly Leu Asp
290                 295                 300

Glu Asp Ser Asp Arg Ala Ile Glu Gly Arg Thr Ala Thr Ser Glu Tyr
305                 310                 315                 320

Gln Thr Phe Phe Asn Pro Arg Thr Phe Gly Ser Gly Glu Ala Asp Cys
                325                 330                 335

Gly Leu Arg Pro Leu Phe Glu Lys Lys Ser Leu Glu Asp Lys Thr Glu
                340                 345                 350

Arg Glu Leu Leu Glu Ser Tyr Ile Asp Gly Arg Ile Val Glu Gly Ser
                355                 360                 365

Asp Ala Glu Ile Gly Met Ser Pro Trp Gln Val Met Leu Phe Arg Lys
370                 375                 380

Ser Pro Gln Glu Leu Leu Cys Gly Ala Ser Leu Ile Ser Asp Arg Trp
385                 390                 395                 400

Val Leu Thr Ala Ala His Cys Leu Leu Tyr Pro Pro Trp Asp Lys Asn
                405                 410                 415

Phe Thr Glu Asn Asp Leu Leu Val Arg Ile Gly Lys His Ser Arg Thr
                420                 425                 430

Arg Tyr Glu Arg Asn Ile Glu Lys Ile Ser Met Leu Glu Lys Ile Tyr
                435                 440                 445

Ile His Pro Arg Tyr Asn Trp Arg Glu Asn Leu Asp Arg Asp Ile Ala
        450                 455                 460

Leu Met Lys Leu Lys Lys Pro Val Ala Phe Ser Asp Tyr Ile His Pro
465                 470                 475                 480
```

-continued

```
Val Cys Leu Pro Asp Arg Glu Thr Ala Ala Ser Leu Leu Gln Ala Gly
                485                 490                 495

Tyr Lys Gly Arg Val Thr Gly Trp Gly Asn Leu Lys Glu Thr Trp Thr
            500                 505                 510
Ala Asn Val Gly Lys Gly Gln Pro Ser Val Leu Gln Val Val Asn Leu
        515                 520                 525
Pro Ile Val Glu Arg Pro Val Cys Lys Asp Ser Thr Arg Ile Arg Ile
    530                 535                 540
Thr Asp Asn Met Phe Cys Ala Gly Tyr Lys Pro Asp Glu Gly Lys Arg
545                 550                 555                 560
Gly Asp Ala Cys Glu Gly Asp Ser Gly Gly Pro Phe Val Met Lys Ser
                565                 570                 575

Pro Phe Asn Asn Arg Trp Tyr Gln Met Gly Ile Val Ser Trp Gly Glu
            580                 585                 590
Gly Cys Asp Arg Asp Gly Lys Tyr Gly Phe Tyr Thr His Val Phe Arg
        595                 600                 605

Leu Lys Lys Trp Ile Gln Lys Val Ile Asp Gln Phe Gly Glu
    610                 615                 620
```